(12) United States Patent
Schiemann et al.

(10) Patent No.: US 8,198,452 B2
(45) Date of Patent: Jun. 12, 2012

(54) POLYMORPHIC FORMS AND PROCESS

(75) Inventors: Kai Schiemann, Seeheim-Jugenheim (DE); Ulrich Emde, Darmstadt (DE); Tobias Schlueter, Weiterstadt (DE); Christoph Saal, Otzberg (DE); Michael Maiwald, Darmstadt (DE)

(73) Assignee: Merck Patent Gesellschaft MIT Beschränkter Haftung, Darmstadt (DE)

( * ) Notice: Subject to any disclaimer, the term of this patent is extended or adjusted under 35 U.S.C. 154(b) by 699 days.

(21) Appl. No.: 12/305,524

(22) PCT Filed: May 26, 2007

(86) PCT No.: PCT/EP2007/004711
§ 371 (c)(1),
(2), (4) Date: Dec. 18, 2008

(87) PCT Pub. No.: WO2007/147480
PCT Pub. Date: Dec. 27, 2007

(65) Prior Publication Data
US 2009/0176820 A1   Jul. 9, 2009

(30) Foreign Application Priority Data
Jun. 19, 2006 (EP) .................... 06012525

(51) Int. Cl.
*C07D 401/00* (2006.01)
*A61K 31/445* (2006.01)
(52) U.S. Cl. ..................... 546/196; 514/320
(58) Field of Classification Search .......... None
See application file for complete search history.

(56) References Cited

FOREIGN PATENT DOCUMENTS
WO   WO 2005/063735 A1   7/2005

OTHER PUBLICATIONS

Vippagunta, S., et al., Adv. Drug Deliv. Rev., vol. 48, 2001, pp. 3-26.*
E. L. Eliel et al., "Stereochemistry of Organic Compounds", John Wiley & Sons, Inc. (1994) XP002459712 pp. 322-336.

* cited by examiner

*Primary Examiner* — Janet Andres
*Assistant Examiner* — Heidi Reese
(74) *Attorney, Agent, or Firm* — Millen, White, Zelano & Branigan, P.C.

(57) ABSTRACT

The invention relates to a process for the manufacture of enantiomerically enriched or pure compounds of formula I

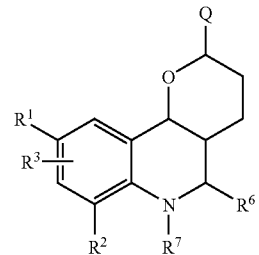

wherein $R^1$, $R^2$, $R^3$, $R^6$, $R^7$ and Q are defined as in claim 1 as well as their crystalline forms for the treatment of proliferative diseases such as cancer.

21 Claims, 9 Drawing Sheets

Figure 1: XRPD, Form A1
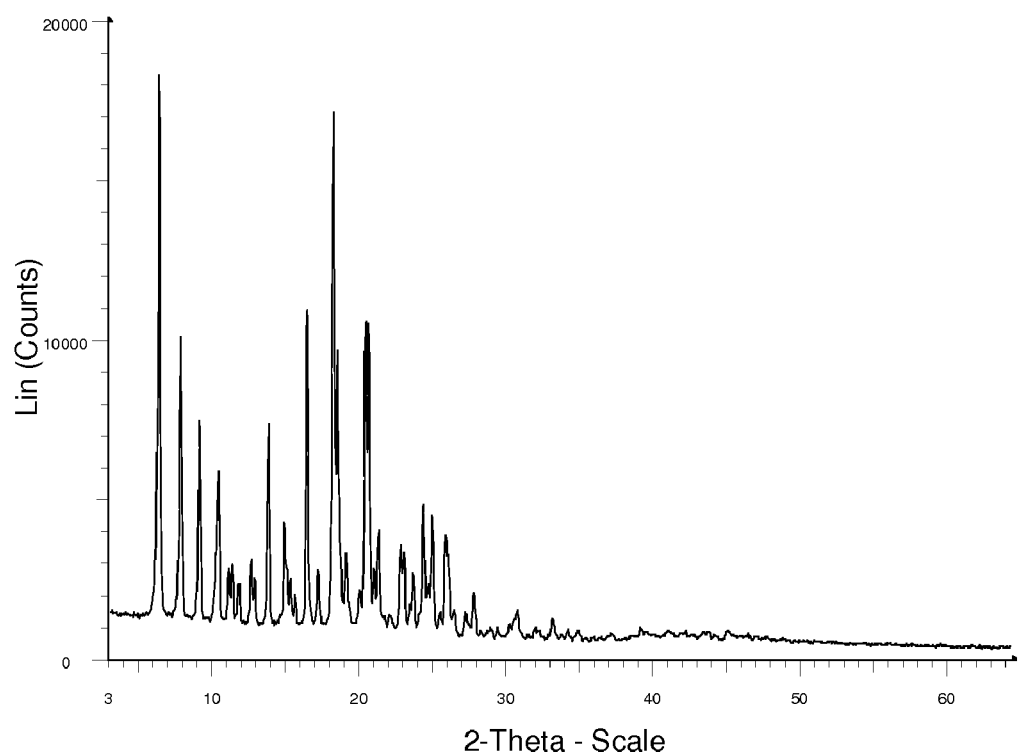

Figure 2: XRPD, Form A2
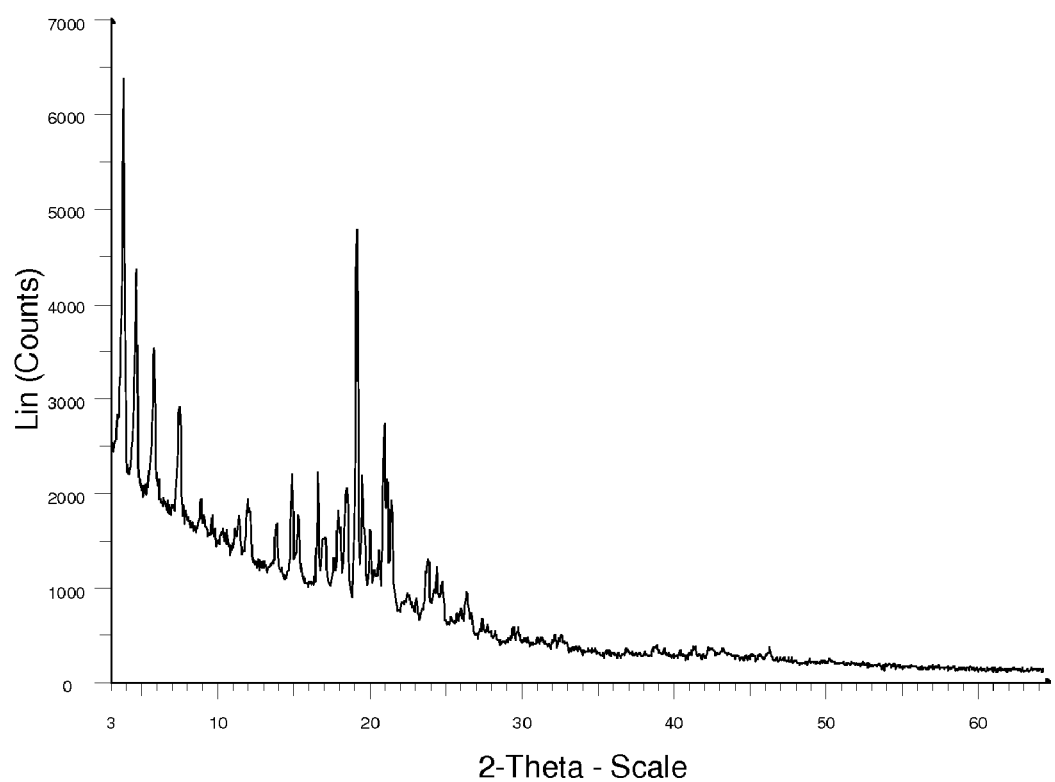

Figure 3: XRPD, Form A3
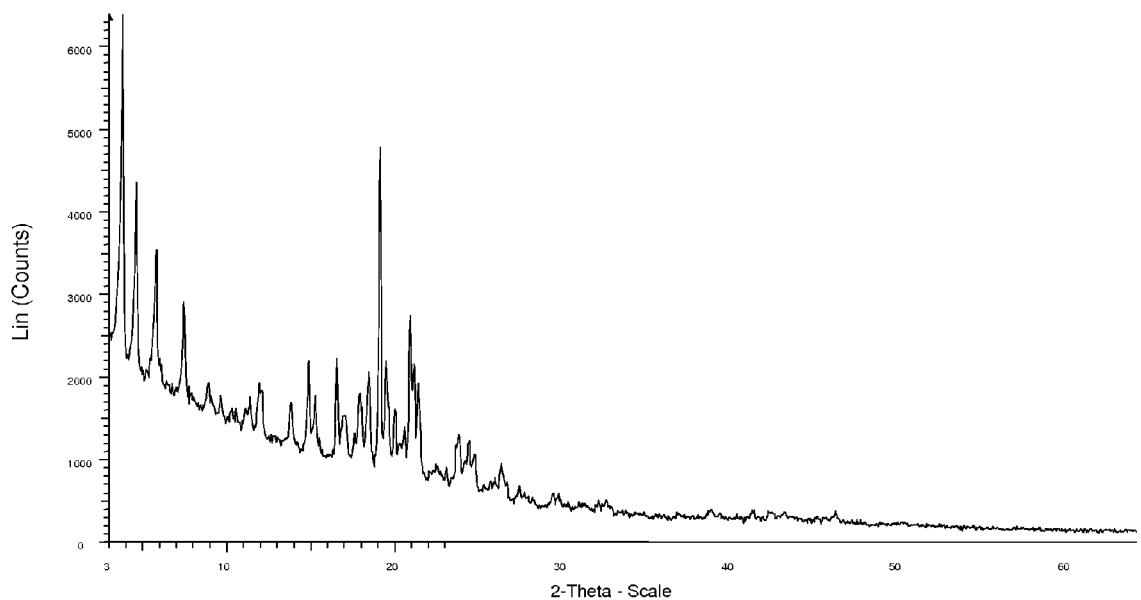

Figure 4: Raman-Spectrum, Form A1
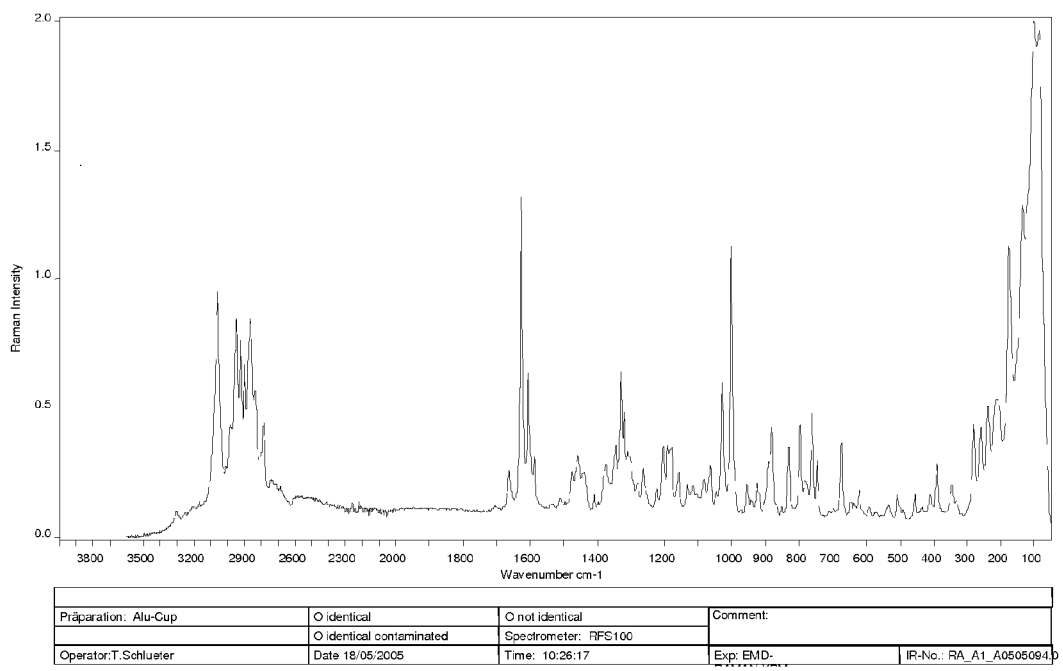

Figure 5: Raman-Spectrum, Form A2
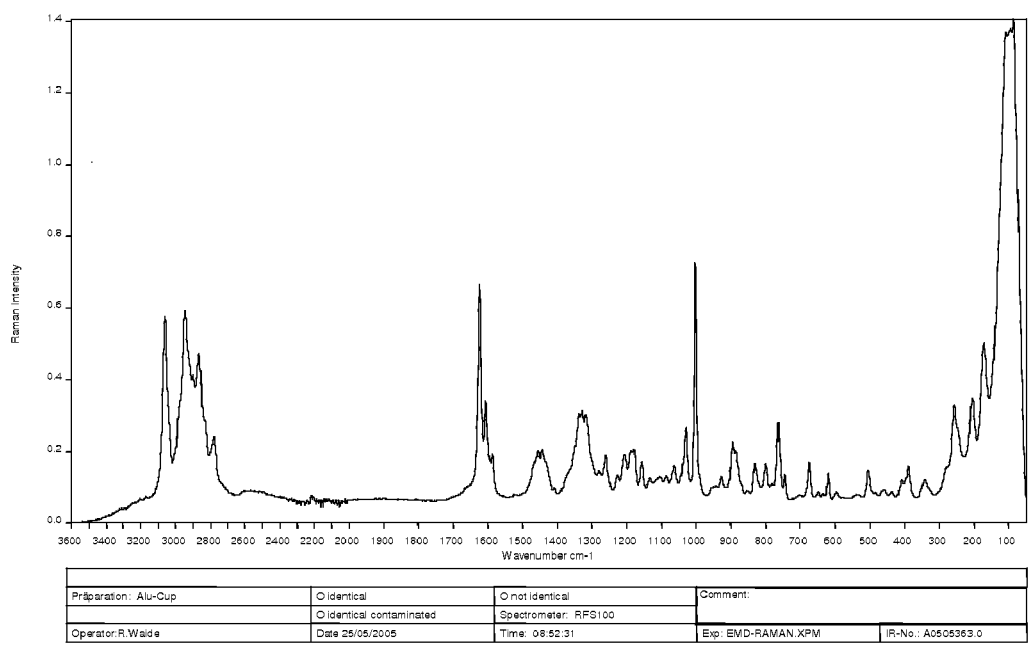

Figure 6: Raman Spectrum Form A3
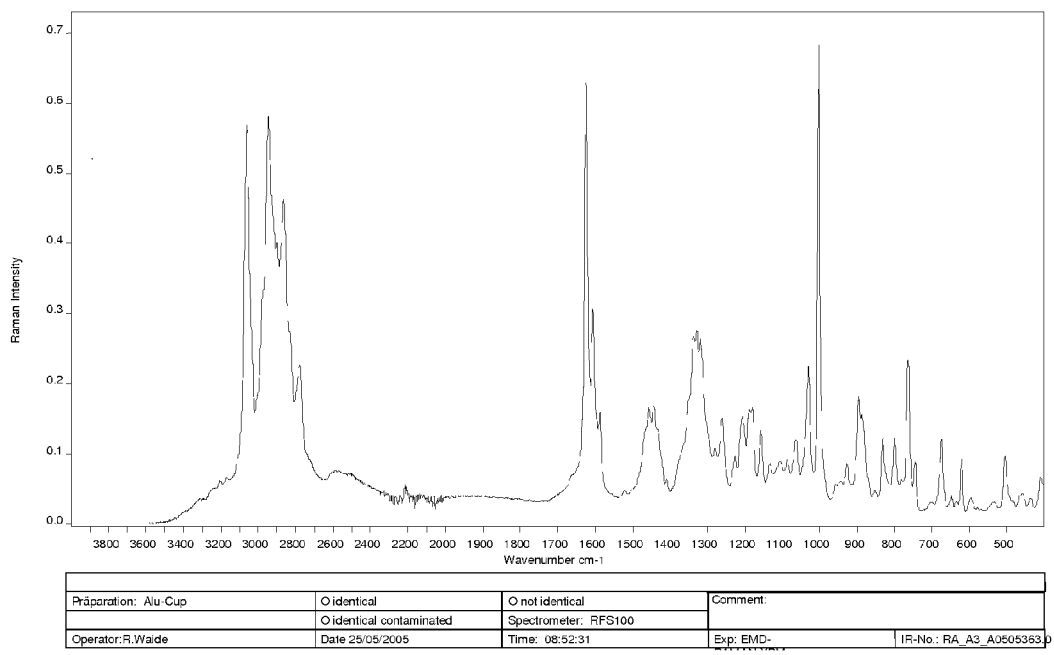

Figure 7: IR-Spectrum, Form A1
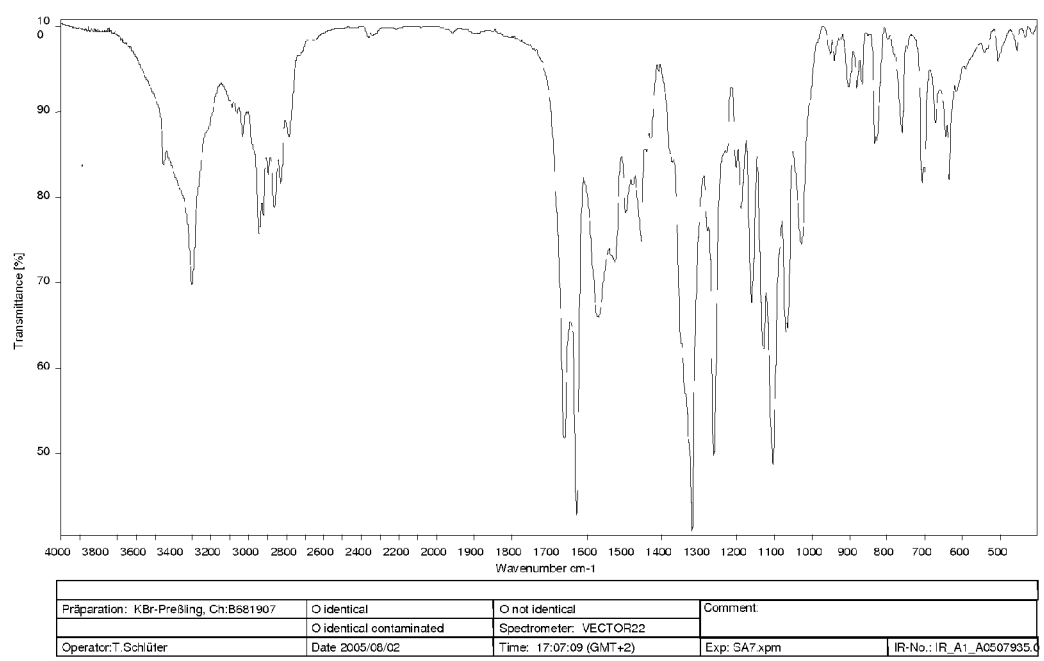

Figure 8: IR-Spectrum, Form A2
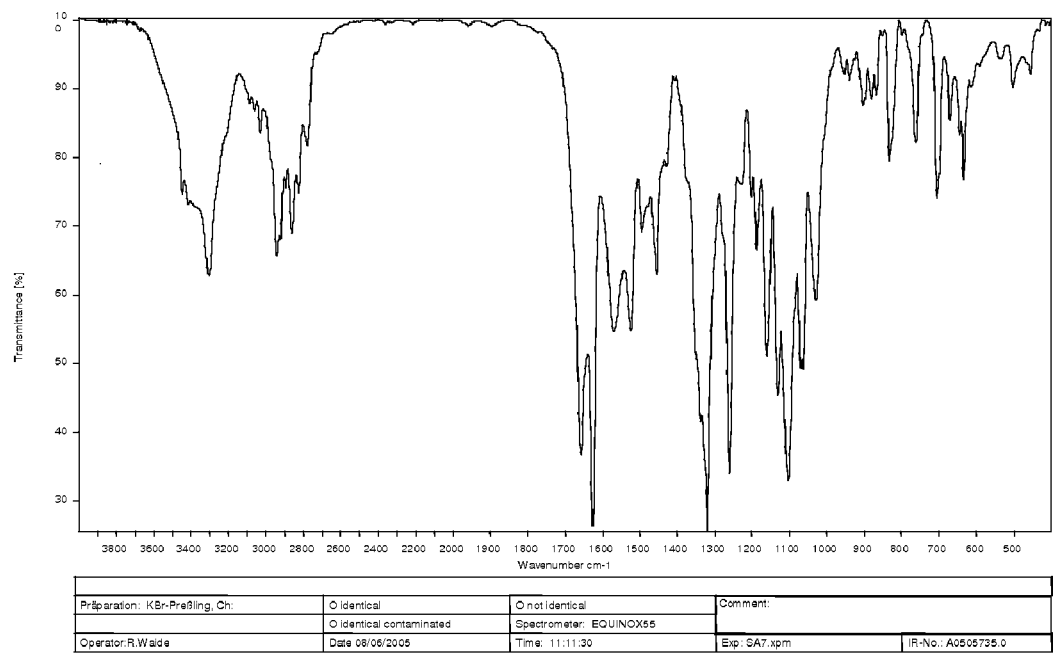

Figure 9: IR Spectrum Form A3
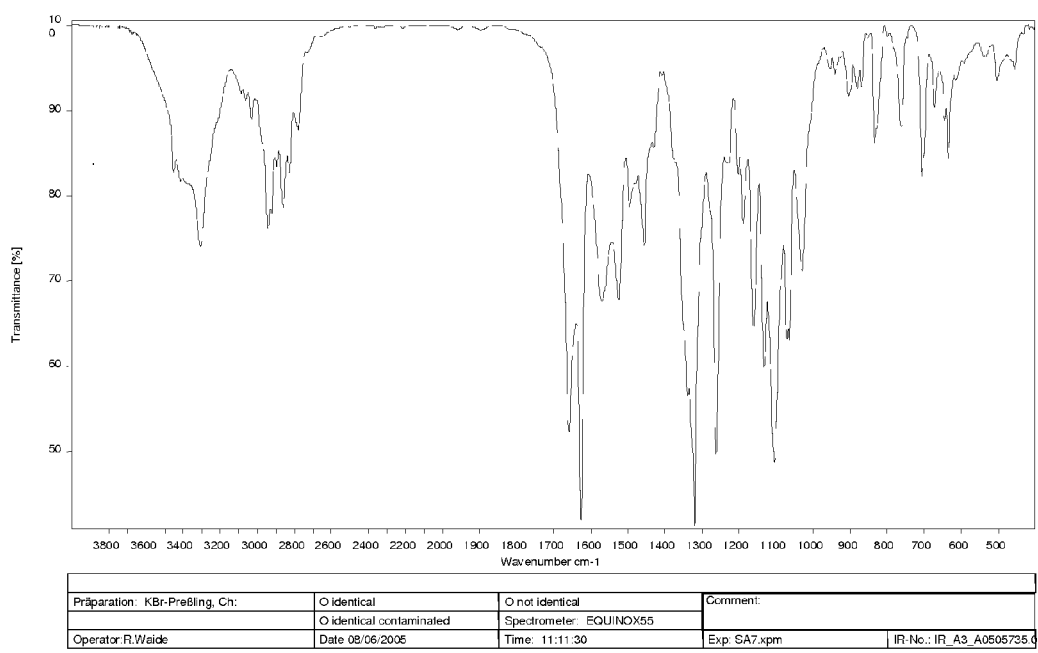

POLYMORPHIC FORMS AND PROCESS

The invention relates to a process for the manufacture of enantiomerically enriched or pure compounds of formula I

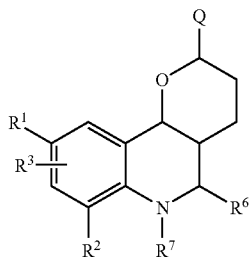

wherein
$R^1$, $R^2$, $R^3$ independently of one another is H, A, Aryl, Heteroaryl, Hal, —(CY$_2$)$_n$—SA, —(CY$_2$)$_n$—SCF$_3$, —(CY$_2$)$_n$—SCN, —(CY$_2$)$_n$—CF$_3$, —(CY$_2$)$_n$—OCF$_3$, R, Cycloalkyl, —SCH$_3$, —SCN, —CF$_3$, —OCF$_3$, —OA, —(CY$_2$)$_n$—OH, —(CY$_2$)$_n$—CO$_2$R, —(CY$_2$)$_n$—CN, —(CY$_2$)$_n$-Hal, —(CY$_2$)$_n$—NR$_2$, (CY$_2$)$_n$—OA, (CY$_2$)$_n$—OCOA, —SCF$_3$, (CY$_2$)$_n$—CONR$_2$, —(CY$_2$)$_n$—NHCOA, —(CY$_2$)$_n$—NHSO$_2$A, SF$_5$, Si(CH$_3$)$_3$, CO—(CY$_2$)$_n$—CH$_3$, —(CY$_2$)$_n$—N-Pyrrolidon, (CH$_2$)$_n$NRCOOR, NRCOOR, NCO, (CH$_2$)$_n$COOR, NCOOR, (CH$_2$)$_n$OH, NR(CH$_2$)$_n$NR$_2$, C(OH)R$_2$, NR(CH$_2$)$_n$OR, NCOR, (CH$_2$)$_n$Aryl, (CH$_2$)$_n$Heteroaryl, (CH$_2$)$_n$R$^1$, (CH$_2$)$_n$X(CH$_2$)$_n$Aryl, (CH$_2$)$_n$X(CH$_2$)$_n$Heteroaryl, (CH$_2$)$_n$CONR$_2$, XCONR(CH$_2$)$_n$NR$_2$, N[(CH$_2$)$_n$XCOOR]CO(CH$_2$)$_n$Aryl, N[(CH$_2$)$_n$XR]CO(CH$_2$)$_n$Aryl, N[(CH$_2$)$_n$XR]CO(CH$_2$)$_n$XAryl, N[(CH$_2$)$_n$XR]SO$_2$(CH$_2$)$_n$Aryl, N[(CH$_2$)$_n$NRCOOR]CO(CH$_2$)$_n$Aryl, N[(CH$_2$)$_n$NR$_2$]CO(CH$_2$)$_n$Aryl, N[(CH$_2$)$_n$NR$_2$]CO(CH$_2$)$_n$NRAryl, N[(CH$_2$)$_n$NR$_2$]SO$_2$(CH$_2$)$_n$Aryl, N[(CH$_2$)$_n$XR]CO(CH$_2$)$_n$Heteroaryl, N[(CH$_2$)$_n$XR]CO(CH$_2$)$_n$XHeteroaryl, N[(CH$_2$)$_n$XR]SO$_2$(CH$_2$)$_n$Heteroaryl, N[(CH$_2$)$_n$NRCOOR]CO(CH$_2$)$_n$Heteroaryl, N[(CH$_2$)$_n$NR$_2$]CO(CH$_2$)$_n$Heteroaryl, N[(CH$_2$)$_n$NR$_2$]CO(CH$_2$)$_n$NRHeteroaryl and wherein, R$^1$ and R$^3$ together also may be —N=C(CF$_3$)=N—, —N—CR=N— or —N—N=N— and wherein non-adjacent groups CY$_2$ can be replaced by X
Y is H, A, Hal, OR, E-R$^1$,
E is —NR$^1$SO$_2$—, —NR$^1$CO—, NR$^1$CONR$^1$—, —NR$^1$COO—, —NR$^1$CS—, —NR$^1$CSNR$^1$—, —NR$^1$COS—, NR$^1$CSO—, —NR$^1$CSS or —NR$^1$—
A is Alkyl or Cycloalkyl, wherein one or more H-atoms can be replaced by Hal,
Hal is F, Cl, Br or I
R is H or A, in the case of geminal groups R together also —(CH$_2$)$_5$—, —(CH$_2$)$_4$— or —(CH$_2$)$_n$—X—(CH$_2$)$_n$, or —(CH$_2$)$_n$—Z—(CH$_2$)$_n$,
X is O, S or NR$^1$,
Q is CH$_2$-E-(CH$_2$)$_p$R$^1$,
Z is CH$_2$, X, CHCONH$_2$, CH(CH$_2$)$_n$NR$^1$COOR$^1$, CHNR$^1$COOR$^1$, NCHO, CHCON(R$^1$)$_2$, CH(CH$_2$)$_n$COOR$^1$, NCOOR$^1$, CH(CH$_2$)$_n$OH, N(CH$_2$)$_n$OH, CHNH$_2$, CH(CH$_2$)$_n$NR$^1$$_2$, CH(CH$_2$)$_n$NR$^1$$_2$, C(OH)R$^1$, CHNCOR$^1$, NCOR$^1$, N(CH$_2$)$_n$Aryl, N(CH$_2$)$_n$Heteroaryl, CHR$^1$, NR$^1$, CH(CH$_2$)$_n$Aryl, CH(CH$_2$)$_n$Heteroaryl, CH(CH$_2$)$_n$R$^1$, N(CH$_2$)$_n$COOR$^1$, CH(CH$_2$)$_n$X(CH$_2$)$_n$Aryl, CH(CH$_2$)$_n$X(CH$_2$)$_n$Heteroaryl, N(CH$_2$)$_n$CON(R$^1$)$_2$, NSO$_2$R$^1$, CHSO$_2$N(R$^1$)$_2$, XCONR(CH$_2$)$_n$N(R$^1$)$_2$, NCO(CH$_2$)$_n$Aryl, NCO(CH$_2$)$_n$XAryl, NSO$_2$(CH$_2$)$_n$Aryl, NCO(CH$_2$)$_n$Aryl, NCO(CH$_2$)$_n$NR$^1$Aryl, NCO(CH$_2$)$_n$Heteroaryl, NCO(CH$_2$)$_n$XHeteroaryl, NSO$_2$(CH$_2$)$_n$Heteroaryl, NCO(CH$_2$)$_n$NR$^1$Heteroaryl, N(CH$_2$)$_n$NR$_2$CH, CHO(CH$_2$)$_n$N(R$^1$)$_2$, CHX(CH$_2$)$_n$N(R$^1$)$_2$, NCO(CH$_2$)$_n$NR$_2$,
R$^6$ is unsubstituted Aryl or Heteroaryl or Aryl or Heteroaryl which is substituted in at least one position by Hal, NO$_2$, CN, OR, A, —(CY$_2$)$_n$—OR, —OCOR, —(CY$_2$), —CO$_2$R, —(CY$_2$), —CN, —NCOR, —COR oder —(CY$_2$), —NR$_2$ or by Aryl or Heteroaryl which also may be substituted by Hal, NO$_2$, CN, A, OR, OCOR, COR, NR$_2$, CF$_3$, OCF$_3$, OCH(CF$_3$)$_2$,
R$^7$ is (C=O)—R, (C=O)—NR$_2$, (C=O)—OR, H or A
and
n is 0, 1, 2, 3, 4, 5, 6 or 7
p is 0, 1, 2, 3, 4, or 5, preferred 1 or 2
s is 0, 1, 2, 3 or 4, particularly 0
as well as their pharmaceutically acceptable derivatives, solvates, tautomeres, salts and polymorphic forms.

Preferred compounds of formula I are those of formula I1

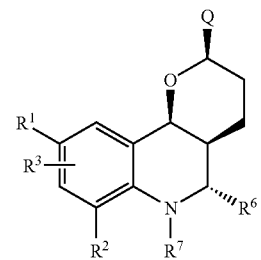

wherein R$^1$ to R$^6$ and Q has the meaning given above.

The compounds of the present invention are used for the treatment and prophylaxis of diseases that are influenced by inhibition, regulation and/or modulation of the mitotic motor proteins, especially the mitotic motor protein Eg5. These are predominantely all types of cancer and other neoplastic diseases.

Similar compounds to those obtained by the present invention are e.g. disclosed in WO 2005/063735.

The compounds of the formula I and salts thereof are obtained by the following process, characterised in that a compound of the formula A

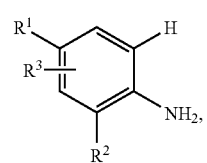

in which R$^1$, R$^2$ and R$^3$ have the meanings indicated above, is reacted with a compound of the formula B

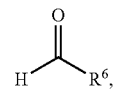

in which
R⁶ has the meaning indicated above,
and
with a compound of the formula C,

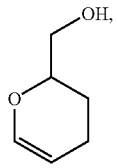

C preferably in the presence of a suitable solvent, preferably acetonitrile and a protonic acid or Lewis acid, such as, for example, trifluoroacetic acid, hexafluoroisopropanol, bismuth(II) chloride, ytterbium(II) triflate, scandium(III) triflate or cerium(IV) ammonium nitrate, preferably trifluoroacetic acid,
a radical other than H is optionally introduced by conventional methods for R⁷, and in that the resulting alcohol is transformed into a leaving group, such as mesyl, tosyl, benzenesulfonyl, trifluormethysulfonyl, nonafluorbutylsulfonyl, Cl, Br or I, preferably mesyl, and further transformed in the amino derivatives of formula I by reaction with a suitable group containing an NH moiety, such as NH³ or HN(R¹)₂. The amino derivatives and preferably the compounds of formula I, wherein Q is $CH_2NH_2$, are then subjected to a deracemization step and further transformation into the other compounds of formula I by known procedures, such as alkylation, or acylation.

Surprisingly, it has been found that a racemic or non enantiomerically pure compound of formula I, and especially a compound of formula I, wherein Q is $CH_2NH_2$, form complexes with enantiomerically pure tartaric acid derivatives, preferably benzoyl tartaric acid and especially (2R,3R)-(–)-Di-O-benzoyl tartaric acid, which crystallize with high enantiomeric purity.

After separation of the crystalline phase from a suitable solvent, preferably polar protic solvents, such as alcohols, their mixtures or alcohol/water mixtures, the enantiomerically further enriched or pure compound of formula I can be obtained from the complex by reaction with a base, such as alkali hydroxide, preferably sodium hydroxide. The enantiomerically enriched or pure compounds of formula I, wherein Q is other than $CH_2NH_2$ are then obtained by standard synthesis starting from the enriched or pure compounds of formula I, wherein Q is $CH_2NH_2$.

Thus, the invention relates preferably to a process for the manufacture of enantiomerically enriched or pure compounds of formula I, comprising the following steps:
a) a racemic or non enantiomerically pure compound of formula I is reacted with a enantiomerically pure tartaric acid derivative, in a suitable solvent, preferably inorganic solvent, such that a crystalline complex is formed
b) the complex formed in step a) is isolated and treated with a base
and optionally
c) the enantiomerically further enriched or pure compound of formula I wherein Q is $CH_2NH_2$ is transformed into the further compounds of formula I, wherein Q is other than $CH_2NH_2$ by standard procedures, that transform the primary amino-group.

Standard procedures as defined under c) are e.g. alkylation, amidation, acylation hydroxylation. Preferably a standard procedure is the reaction with carbonyldiimidazole and an amine such as N,N-Diethylethylenediamine.

Above and below, the radicals R, $R^1$, $R^2$, $R^3$, $R^4$, $R^5$, $R^6$, $R^7$, X, Y, Q, Z, m, p and s have the meanings indicated for the formula I, unless expressly indicated otherwise. If individual radicals occur a number of times within a compound, the radicals adopt the meanings indicated, independently of one another.

A denotes alkyl, is preferably unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl. A also denotes cycloalkyl.

Cycloalkyl preferably denotes cyclopropyl, cyclobutyl, cyclopentyl, cyclohexyl or cycloheptyl, but in particular cyclopentyl.

$R^1$ preferably denotes A, $CF_3$, $OCF_3$, SA, SCN, $CH_2CN$, —OCOA, Hal, $SCF_3$, preferably also t-butyl, —CH($CH_3$)$CH_2CH_3$, isopropyl, ethyl or methyl. In particular, $R^1$ denotes t-butyl, isopropyl, ethyl, $CF_3$, methyl, Br, Cl, $SCF_3$, CH($CH_3$)$CH_2CH_3$, n-propyl, $OCH_3$, $SCH_3$, n-butyl, —SCN, $CH_2CN$. $R^1$ particularly preferably denotes t-butyl, isopropyl, ethyl or $CF_3$.

$R^2$ preferably denotes H, Hal, A or OA, in particular Br, cyclopropyl, $OCH_3$. Particular preference is furthermore given to H or F.

$R^3$ preferably denotes H or A, in particular H. $R^3$ is preferably in the 5-position. In particular, $R^3$ denotes H or F.

If the radicals and indices, such as, for example, n, occur more than once, the radicals and indices may, independently of one another, adopt different values.

$R^6$ preferably denotes phenyl, 2-, 3- or 4-pyridyl, pyrimidyl, furyl or thienyl, each of which is unsubstituted or mono- or polysubstituted by Hal, CN, $NO_2$, OH, $CF_3$, $OCH(CF_3)_2$, $OCOCH_3$ or A. $R^6$ is preferably not a heteroaromatic radical. In particular, $R^6$ denotes one of the following groups:

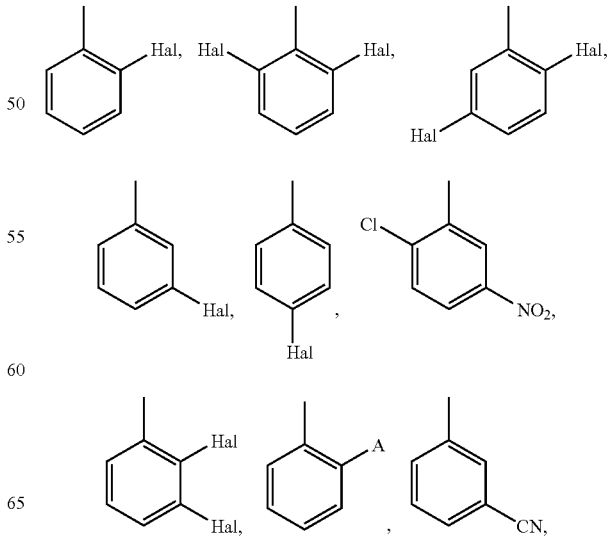

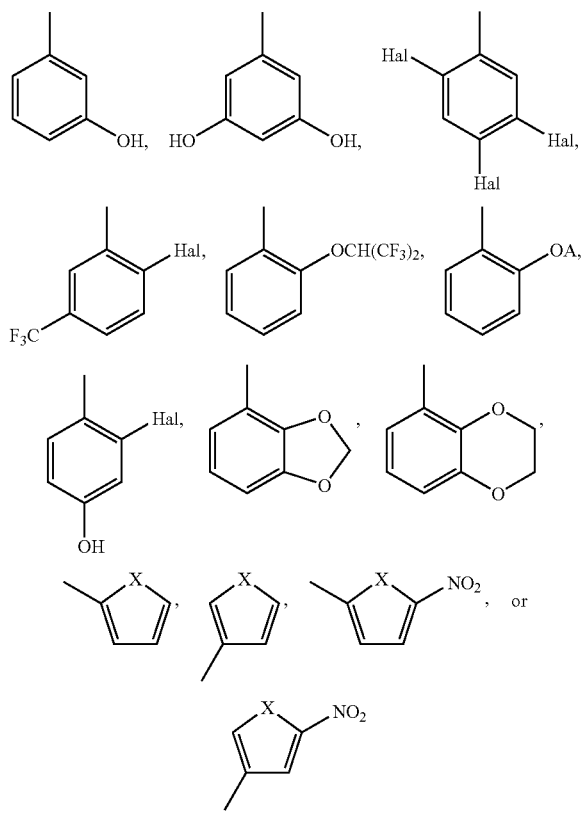

in which

X denotes O, S or NR and in particular O or S, A has the meaning indicated above, but preferably denotes methyl, and Hal preferably denotes F or Cl.

Particular preference is furthermore given to compounds of the formula I in which $R^6$ has one of the following meanings:

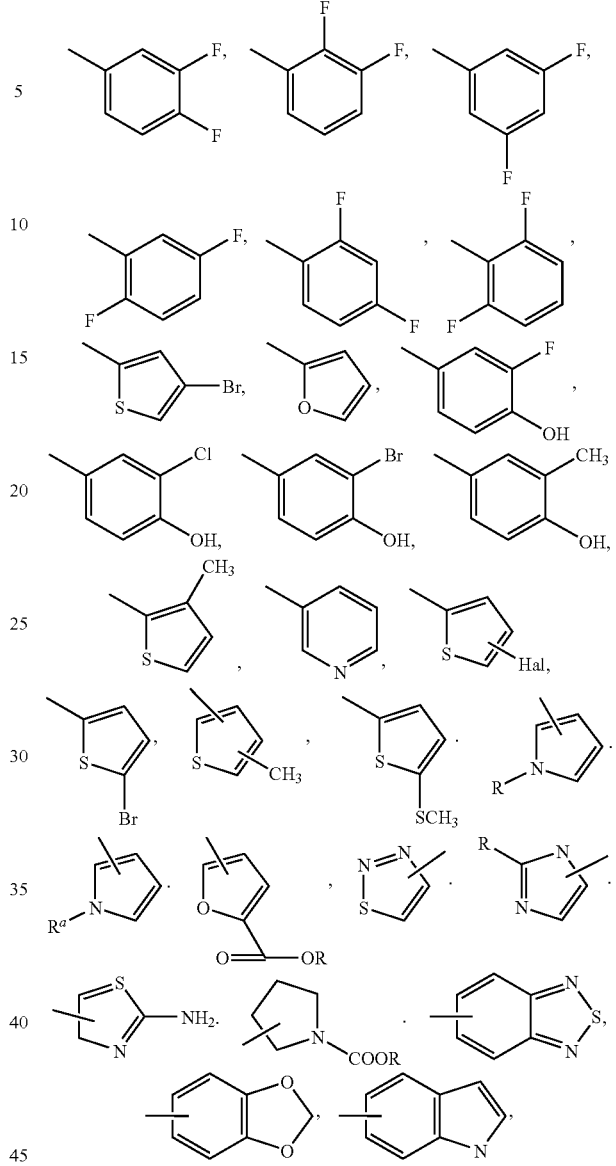

$R^7$ preferably denotes H or A, in particular H.

Aryl preferably denotes phenyl, naphthyl or biphenyl, each of which is un-substituted or mono-, di- or trisubstituted by Hal, A, OH, OA, $NH_2$, $NO_2$, CN, COOH, COOA, $CONH_2$, NHCOA, $NHCONH_2$, $NHSO_2A$, CHO, COA, $SO_2NH_2$, $SO_2A$, —$CH_2$—COOH or —$OCH_2$—COOH.

Aryl preferably denotes phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-methoxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Heteroaryl preferably denotes a mono- or bicyclic aromatic heterocycle having one or more N, O and/or S atoms which is unsubstituted or mono-, di- or trisubstituted by Hal, A, $NO_2$, NHA, $NA_2$, OA, COOA or CN. Heteroaryl particularly preferably denotes a monocyclic saturated or aromatic heterocycle having one N, S or O atom, which may be unsubstituted or mono-, di- or trisubstituted by Hal, A, NHA, $NA_2$, $NO_2$, COOA or benzyl.

Irrespective of further substitutions, unsubstituted heteroaryl denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxan-6-yl, 2,1,3-benzothiadiazol-4- or -5-yl or 2,1,3-benzoxadiazol-5-yl.

Hal preferably denotes F, Cl or Br, but also I, particularly preferably F or Cl.

Throughout the invention, all radicals which occur more than once may be identical or different, i.e. are independent of one another.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use may also be made here of variants known per se which are not mentioned here in greater detail.

If desired, the starting materials may also be formed in situ so that they are not isolated from the reaction mixture, but instead are immediately converted further into the compounds of the formula I.

The reaction is generally carried out in an inert solvent, preferably in the presence of a protonic acid or Lewis acid, such as TFA, HFIP, bismuth(III) salts, ytterbium(III) salts or CAN. Depending on the conditions used, the reaction time is between a few minutes and 14 days, the reaction temperature is between about 0° and 180°, normally between 0° and 100°, particularly preferably between 15° and 35° C.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; nitriles, such as acetonitrile; carbon disulfide; carboxylic acids, such as formic acid or acetic acid; nitro compounds, such as nitromethane or nitrobenzene, or mixtures of the said solvents.

Compounds of the formula I in which $R^7$ has a meaning other than H are preferably prepared by alkylation or acylation from the compounds of the formula I in which $R^7$ denotes H.

If desired, a functionally modified amino and/or hydroxyl group in a compound of the formula I can be liberated by solvolysis or hydrogenolysis by conventional methods. This can be carried out, for example, using NaOH or KOH in water, water/THF or water/dioxane at temperatures between 0 and 100°.

The reduction of an ester to the aldehyde or alcohol or the reduction of a nitrile to the aldehyde or amine is carried out by methods as are known to the person skilled in the art and are described in standard works of organic chemistry.

The invention furthermore relates to medicaments comprising at least one compound of the formula I and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

A therapeutically effective amount of a compound of the formula I depends on a number of factors, including, for example, the age and weight of the animal, the precise condition which requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention also relates to a process for the manufacture of enantiomerically enriched or pure compounds of formula IA which are preferred compounds of formula I and which can serve as intermediates in the process for the manufacture of the enantiomerically enriched or pure compounds of formula I that differ from the compounds of formula IA:

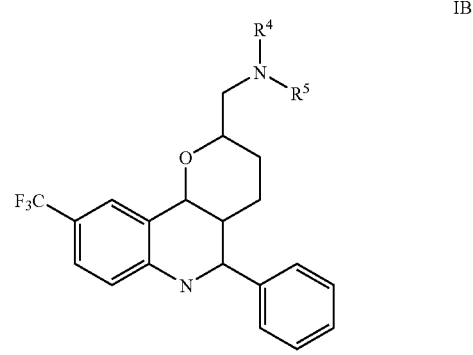

wherein $R^1$, $R^2$, $R^3$ and $R^6$ are as defined above and $R^4$, $R^5$ are independenly of one another T-$(CH_2)_p$—$R^1$, together also —$(CH_2)_5$—, —$(CH_2)$, —X—$(CH_2)_n$— or —$(CH_2)_n$—Z—$(CH_2)_n$—, wherein T is —$SO_2$—, —CO—, —$CONR^1$—, —COO—, —CS—, —$CSNR^1$—, —COS—, —CSO—, —CSS or a single bond, P is 0, 1, 2, 3, 4 or 5, preferably 1 or 2.

n is as defined above.

$R^1$ is preferably A, Cycloalkyl, —$C(CH_3)_3$, —$CF_3$, —$SF_5$, $OCF_3$, Hal, —$(CY_2)$, —$CF_3$, CN. Especially preferred is $CF_3$.

In especially preferred compounds of formula I and IA, $R^2$ is preferably H or Hal, especially H.

$R^3$ is preferably H or Hal, especially H.

$R^4$, $R^5$ is preferably H or A, $CONH(CH_2)_nNA_2$, $SO_2NH(CH_2)_nNA_2$ or $CO(CH_2)_nNA_2$. Especially preferred are compounds of formula I and also IA wherein $R^4$ and $R^5$ are simultaneously H or $R^4$ is H and $R^5$ is A, preferably methyl.

$R^6$ is preferably aryl or hetaryl. Especially preferred is unsubstitued or substituted aryl, preferably phenyl.

Preferred compounds of formula IA are those of formula IA1:

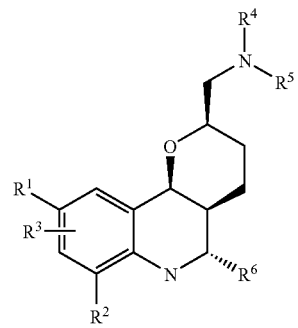

wherein $R^1$, $R^2$, $R^3$, $R^4$, $R^5$ and $R^6$ have the meanings given above.

Especially preferred are compounds of formula IB

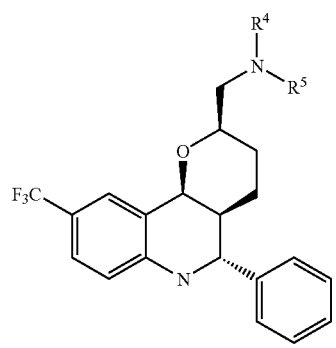

wherein $R^4$ and $R^5$ are as defined above.

Preferred compounds of formula IB are those of formula IB1:

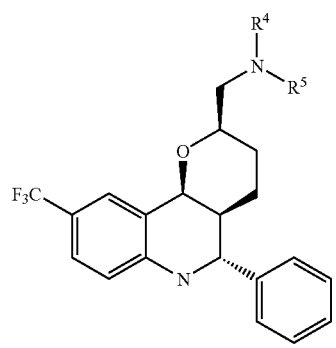

wherein $R^4$ and $R^5$ have the meaning given above.

The intermediates for the inventive manufacturing process, such as compound IA, wherein $R^4$ and $R^5$ are H or A can also be obtained according to WO 2005/063735, especially by reaction of a compound Aa

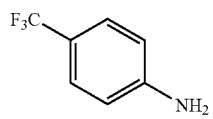

Aa with a compound Ba

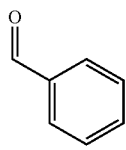

Ba and a compound C

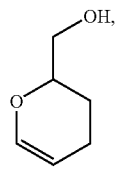

C preferably in the presence of a protonic acid or Lewis acid, such as, for example, trifluoroacetic acid, hexafluoroisopropanol, bismuth(III) chloride, ytterbium(III) triflate, scandium (III) triflate or cerium(IV) ammonium nitrate.

Surprisingly, it has been found that a racemic or non enantiomerically pure compound of formula IA, and especially a compound of formula IA, wherein $R^4$ and $R^5$ are both H, form complexes with enantiomerically pure tartaric acid derivatives, preferably benzoyl tartaric acid and especially (2R,3R)-(−)-Di-O-benzoyl tartaric acid, which crystallize with high enantiomeric purity.

After separation of the crystalline phase from a suitable solvent, the enantiomerically further enriched or pure compound of formula IA can be obtained from the complex by reaction with a base, such as alkali hydroxide, preferably sodium hydroxide. The enantiomerically enriched or pure compounds of formula I are then obtained by standard synthesis starting from the enriched or pure compounds of formula IA.

Thus, the invention relates to a process for the manufacture of enantiomerically enriched or pure compounds of formula I, comprising the following steps:

a) a racemic or non enantiomerically pure compound of formula IA is reacted with a enantiomerically pure tartaric acid derivative in a suitable solvent, preferably inorganic solvent, such that a crystalline complex is formed b) the complex formed in step a) is isolated and treated with a base and optionally c) the enantiomerically further enriched or pure compound of formula IA is transformed into the further compounds of formula I by standard procedures, that transform the primary amino-group.

Standard procedures as defined under c) are e.g. alkylation, amidation, acylation hydroxylation. Preferably, a standard procedure is the reaction with carbonyldiimidazole and an amine such as N,N-Diethylethylenediamine.

In a preferred embodiment of the invention, a racemic or non enantiomerically pure compound of formula IA, wherein $R^4$ and $R^5$ are both H, or wherein $R^4$ is H and $R^5$ is alkyl, preferably methyl, is suspended or dissolved in an organic solvent, such as an alcohol, preferably ethanol at temperatures between 20 and 120° C., preferably between 40 and 90° C. and especially preferred at the boiling point of the solvent at normal pressure.

Upon addition of the tartaric acid the solution is allowed to cool to about room temperature and to stand for a period of a few hours to a few days, preferably about 1 to about 24 hours, especially about 8 to about 20 hours. The crystals are separated and treated with sodium hydroxide to obtain the free base of formula IA.

In an especially preferred embodiment of the present invention, the enantiomerically enriched or pure compound II

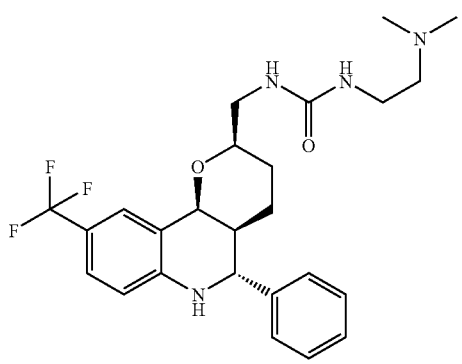

II (1-(2-Dimethylamino-ethyl)-3-((2R,4aS,5R,10bS)-5-phenyl-9-trifluoromethyl-3,4,4a,5,6,10b-hexahydro-2H-pyrano[3,2-c]quinolin-2-ylmethyl)-urea) is obtained by the inventive process.

The term enantiomerically enriched or pure preferably refers to an enantiomeric purity of above 60%, such as about 80% to about 100%. Especially the term refers to an enantiomeric purity of higher than about 98%.

In the most preferred embodiment the present invention relates to the use of a crystalline form of a compound of formula II and its use, for the treatment of proliferative diseases such as cancer, pharmaceutical compositions containing the crystalline form and processes for its preparation.

The compound of formula II as well as therapeutically acceptable salts thereof, are described in WO 2005/063735.

The compound of formula II is therapeutically active and especially useful in the treatment of proliferative diseases.

It has surprisingly been found that the compound of formula II is especially stable in its basic, i.e. non-salt, form and can exist in more than one crystalline form, such as A1, A2 and A3 preferably A1. Another object of the present invention is to provide a process for the preparation of form A1 and A2 and A3, substantially free from other forms of the compound of formula II, such as the amorphous form. X-ray powder diffraction (XRPD) is used as a method of differentiating form A1, A2 and A3 from each other and the non-crystalline or amorphous form of the compound of formula II. Additionally, it is an object of the present invention to provide pharmaceutical formulations comprising a compound of formula I in form A1 or A2 or A3, preferably A1.

Form A1 is a crystalline form which surprisingly exhibits advantageous properties, such as being well-defined, being thermodynamically more stable and less hygroscopic than form A2, A3 and the amorphous form, especially at room temperature. Form A1 also shows a better chemical stability, i.e. proviedes a longer shelf-life based on improved, thermal stability and light stability.

Form A2 and A3 can under certain conditions, completely or partly, be converted into form A1. Form A1 is characterized in being thermodynamically more stable than form A2 and A3.

Form A1 is further characterized as being essentially non-hygroscopic.

Form A1 can be distinguished from form A2, A3 and the amorphous form, using X-ray powder diffraction.

Characterization of form A1, form A2 and A3 can be performed according to standard methods which can be found in e.g. Bunn, C. W. (1948), Chemical Crystallography, Clarendon Press, London; or Klug, H. P. & Alexander, L. E. (1974), X-Ray Diffraction Procedures, John Wiley and Sons, New York.

BRIEF DESCRIPTION OF THE DRAWINGS

FIG. 1 is an X-ray diffraction pattern of polymorphic Form A1;
FIG. 2 is an X-ray diffraction pattern of polymorphic Form A2;
FIG. 3 is an X-ray diffraction pattern of polymorphic Form A3;
FIG. 4 is a Raman-Spectrum of polymorphic Form A1;
FIG. 5 is a Raman-Spectrum of polymorphic Form A2;
FIG. 6 is a Raman-Spectrum of polymorphic Form A3;
FIG. 7 is an IR spectrum of polymorphic Form A1;
FIG. 8 is an IR spectrum of polymorphic Form A2; and
FIG. 9 is an IR spectrum of polymorphic Form A3.

Form A1, according to the present invention, is characterized in providing an X-ray powder diffraction pattern, exhibiting substantially the parameters given in FIG. 1.

According to the invention there is further provided a process for the preparation of form A1, A2 and A3.

Form A1 may be prepared by crystallisation or recrystallizing the compound of formula II of any form, or mixtures of any forms, in an appropriate solvent, such as for instance acetone/water or preferably acetonitril or acetonitril/water, at around room temperature or elevated temperature and for a prolonged time period. Examples of prolonged time periods include, but are not limited to, a few hours, such as 2 hours, up to several weeks. Suitable solvents are, 2-propanol, acetonitrile, tetrahydrofurane, toluol, chloroform, formamide, 2-butanone or pyridine. Acetonitrile is most preferred. Further suitable solvents are supercritical fluids and their modifies. Such solvents are e.g. carbon dioxide, ethylene, propane, butane, dinitrogen oxide ($N_2O$). Suitable modifies are ethanol, methanol or ethyl acetate. Other suitable solvents are consisting of larger molecules, such as transcutol, ethylenglycol, propylenglycol, solutol, capryol PGMC, Capryol 90, long chain aliphatic hydrocarbons, e.g. hexane, octane, decane and long chain alcohols, such as hexanols, octanols, decanols and their esters.

Form A1 may be prepared by suspending the compound of formula II of any form, or mixtures of any forms, in the above solvents and preferably acetonitrile at around room temperature or elevated temperature and for a prolonged time period. Examples of prolonged time periods include, but are not limited to, a few hours, such as 2 hours, up to several weeks. It may also be obtained by dissolving or suspending the compound of formula II of any form, or mixtures of any forms in the pure organic solvent, preferably acetone, at the addition of an anti-solvent, such as water.

Form A2 may be prepared by recrystallizing or suspending the compound of formula II of any form, preferably of A1, or mixtures of any forms, in n-heptane, at around room temperature or elevated temperature and for a prolonged time period. Examples of prolonged time periods include, but are not limited to, a few hours, such as 2 hours, up to several weeks. Form A2 is then obtained by evaporation of the solvent.

Form A3 may be prepared by dispensing the compound of formula II of any form, preferably form A1, in n-heptane followed by stirring at room temperature for 1 to 20 days, preferably 1 to 10 days. Especially preferred are 1 to 5 days. A3 is then isolated by filtration and drying in vacuo.

Form A1 obtained according to the present invention is substantially free from other crystal and non crystalline, i.e. compounds forms of, such as Form A2 or A3. Substantially free from other forms shall be understood to mean that form A1 contains less than 10%, preferably less than 5%, of any other forms, e.g. form A2 and/or A3.

Form A2 obtained according to the present invention is substantially free from other crystal and non crystalline, i.e. compounds forms of, such as Form A1. Substantially free from other forms shall be understood to mean that form A2 contains less than 10%, preferably less than 5%, of any other forms, e.g. form A1.

The present invention also relates to mixtures comprising form A1 in mixture with other solid forms of the compound of formula II. Such mixtures comprise preferably more than 50% by weight of form A1. Other embodiments include for instance mixtures containing a detectable amount of form A, 1%, 2%, 5%, 10%, 20%, 30%, 40%, 50%, 60%, 70%, 80%, 90%, 95%, 98% or 99% (by weight), of form A1.

Examples of other solid forms of include, but are not limited to, form A2, A3 and an amorphous form. The amorphous form was found after recrystallization from DMF (dimethylformamide), DMSO, acetic acid and aqueous solutions at pH 0-pH 6.

A detectable amount of form A1, A2 and A3 is an amount that can be detected using conventional techniques, such as FT-IR, Raman spectroscopy, XRPD and the like.

The expression chemical stability includes, but is not limited to, thermal stability and light stability.

The polymorphic forms of the invention, i.e. form A1, A2 and A3, prepared according to the present invention are analyzed, characterized and differentiated from each other and the amorphous form by X-ray powder diffraction, a technique which is known per se. Another suitable technique to analyze, characterize and differentiate the individual forms is by Raman or IR spectroscopy.

The compounds of formula II also form stable solvates with various solvents. The individual solvates are another object of the present invention. The solvates are obtained by crystallization in the respective solvent, without addition of anti-solvent such as water. Preferred solvents for the manufacture of the solvates of the present invention are methyl tert-butylether (MTBE), acetone and ethylacetate.

Further preferred solvents for the manfucature of the novel solvates are ethanol, 1-propanol, 1-butanol and isobutylmethylketone (IBMK). Other solvates are obtained by use of the following solvents: Anisole, 2-butanole, butyl acetate, cumene, ethyl ether, ethyl formiate, formic acid, isobutyl acetate, isopropyl acetate, methyl acetate, 3-methyl-1-butanol, methyl ethylketone, pentane, 1-pentanole, 2-pentanole, propyl acetate.

Any suitable route of administration may be employed for providing the patient with an effective dosage of form A1, A2 or A3 according to the invention. For example, peroral or parenteral formulations and the like may be employed. Dosage forms include capsules, tablets, dispersions, suspensions and the like, e.g. enteric-coated capsules and/or tablets, capsules and/or tablets containing enteric-coated pellets of. In all dosage forms, the compounds of the formula II in form A1, A2 and A3 can be admixtured with other suitable constituents.

According to the invention, there is further provided a pharmaceutical composition comprising form A1, A2, or A3 preferably A1, as active ingredient, in association with a pharmaceutically acceptable carrier, diluent or excipient and optionally other therapeutic ingredients. Compositions comprising other therapeutic ingredients are especially of interest in the treatment of proliferative diseases, such as cancer. The invention also provides the use of form A1, A2 or A3 preferably A1 in the manufacture of a medicament for use in the treatment of proliferative diseases, such as cancer and related disorders and conditions and a method of treating the diseases, disorders or conditions which method comprises administering to a subject suffering from said condition a therapeutically effective amount of form A1, A2 or A3.

The compositions of the invention include compositions suitable for peroral or parenteral administration. The compositions may be conveniently presented in unit dosage forms, and prepared by any methods known in the art of pharmacy.

In the practice of the invention, the most suitable route of administration as well as the magnitude of a therapeutic dose of form A1, A2 and A3 in any given case will depend on the nature and severity of the disease to be treated. The dose, and dose frequency, may also vary according to the age, body weight, and response of the individual patient.

The compound of the invention may be combined as the active component in intimate admixture with a pharmaceutical carrier according to conventional techniques, such as the oral formulations.

Combination therapies comprising the compound of formula II and other active pharmaceutical ingredients are disclosed in WO 2005/063735.

The respective combinations or mixtures of the compound of formula II and other active pharmaceutical ingredients are also applicable to the compound of formula II in form A1, A2 and A3.

The examples which follow will further illustrate the preparation of the compound of the invention but are not intended to limit the scope of the invention as defined hereinabove or as claimed below.

EXAMPLE 1

Synthesis of 1-(2-Dimethylamino-ethyl)-3-((2R,4aS,5R,10bS)-5-phenyl-9-trifluoromethyl-3,4,4a,5,6,10b-hexahydro-2H-pyrano[3,2-c]quinolin-2-ylmethyl)-urea

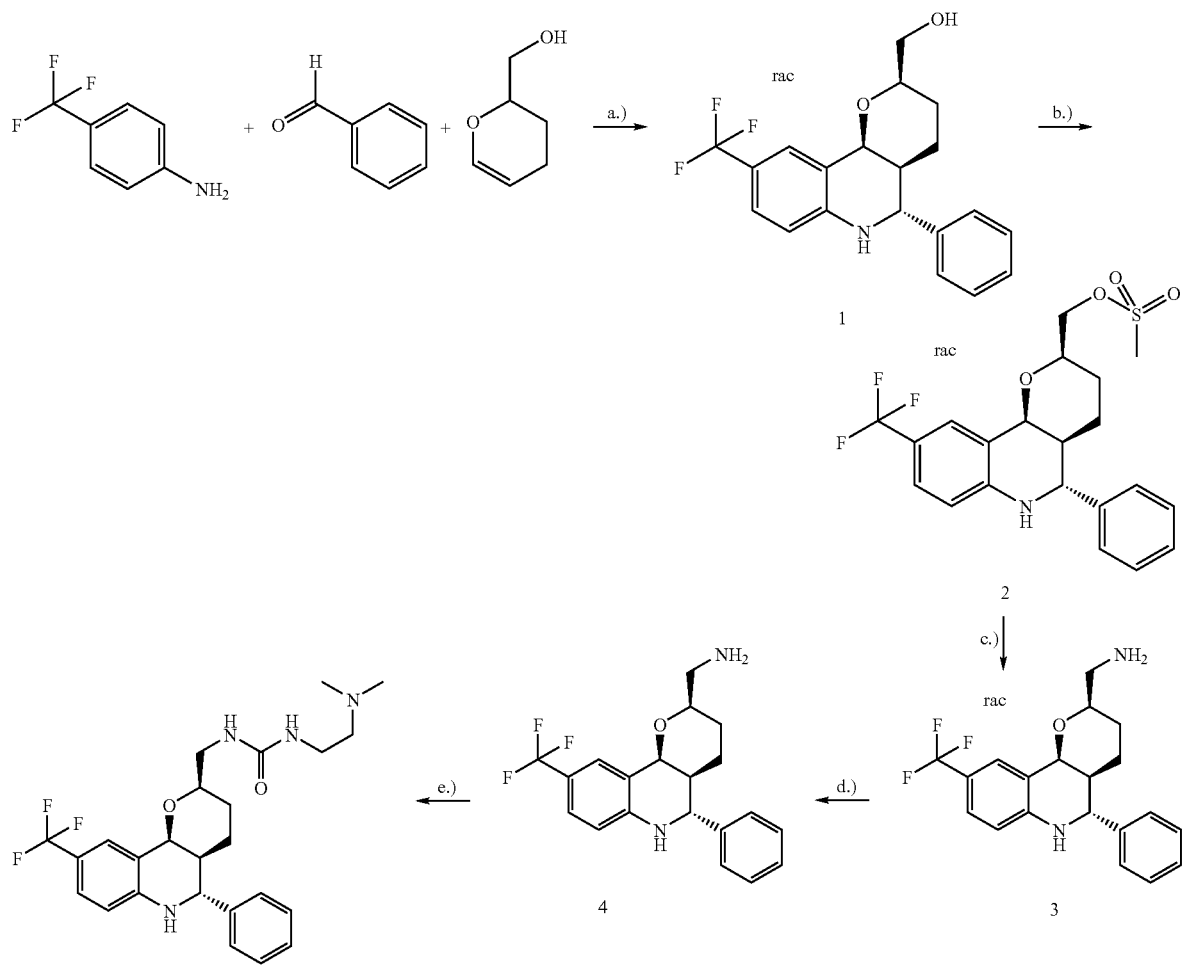

a.)

To a solution of 4-aminobenzotrifluoride (5.00 kg, 31.0 mol) in 10 L acetonitrile was added under intensive cooling in an ice bath trifluoroacetic acid (2.39 L, 31.0 mol) over a period of 20 min. In a second vessel 3,4-dihydro-2H-pyran-2-methanol (3.61 kg, 31.0 mol) and benzaldehyde (3.19 kg, 31 mol) were dissolved in 5 L acetonitrile and cooled to 10° C. To this solution the previously prepared TFA-salt of 4-aminobenzotrifluoride was added over a period of 30 min keeping the temperature below 15° C. The mixture was stirred for 14 h at 25° C., cooled to 15° C. and the precipitate formed was filtered off and washed with 2.5 L acetonitrile (3.36 kg yellow crystals).

To the crude product 12 L THF were added, heated to reflux and filtered at 50° C. 1.96 kg (5.39 kg, 17%) of yellow crystals identified as a single trans-Isomer 1 were obtained. Analytics: m.p.: 282-283° C.

The filtrate was concentrated to a volume of 3 L, cooled to 4° C. and the crystals formed overnight were filtered off (340 g of yellow crystals, identified as 1:1 mixture of cis and trans isomers).

The filtrate was treated with 4 L of petrol ether, cooled to 4° C. overnight, the crystals formed were filtered off, washed with diethyl ether and dried. 524 g (1.44 mol, 5%) of greenish crystals found to be a cis-Isomer were obtained.

b.)

Compound 1 (330 g, 0.91 mol) was suspended in 10 L of DCM. To this suspension triethyl amine (208 mL, 1.50 mmol) and methanesulfonyl chloride (101 mL, 1.30 mol), dissolved in 200 mL of DCM, were added at 22° C. During the addition the temperature increased to 30° C. and the mixture turned clear after 1 h at RT. It was stirred at RT overnight and the solution was poured onto ice water. The organic layer was separated and washed with water 3 times. It was dried over sodium sulfate, filtered and the solvent was evaporated. The crude product was redissolved/suspended in hot ethanol (0.5 L), stirred for 2 h and cooled to 4° C. overnight. The precipitate was filtered off and dried. 383 g (0.87 mol, 96%) of a colorless solid 2 were obtained.

c.)

In an autoclave 3.00 g (6.80 mmol) mesylate 2 was dissolved in 30 mL of methanol. The reaction mixture was stirred and the autoclave cooled and flushed with ammonia gas. The gas inside the autoclave was removed by reduced pressure. The autoclave was again flushed with ammonia gas. The ammonia pressure was allowed to rise to 5 bar. The temperature was brought up to 100° C. and the reaction mixture was stirred overnight. During the reaction the product precipitated. The autoclave was cooled down and decompressed. The reaction mixture was collected, 100 mL methanol was added and cooled down to 0° C. The resulting crystals were collected by filtration to afford 2.14 g (5.91 mmol, 87%) amine 3, which was directly used for the next step without further purification.

d.)

7.18 g (19.8 mmol) racemic amine 3 was suspended in 200 mL ethanol and heated to reflux. 3.55 g (9.9 mmol) (2R,3R)-(−)-Di-O-benzoyl tartaric acid and 20 mL ethanol were added and the solution heated to reflux. The solution was filtered and the filter washed with 30 mL ethanol. The filtrate was allowed to stand for about 18 h at room temperature. During that time precipitation started. The crystals were collected by filtration, washed with a little amount of cold ethanol and then air-dried to give 3.53 g (3.3 mmol, 33%) of the diamine tartaric acid salt. Analytics: m.p.: 169-171° C.; $[\alpha]_D^{20}$=−101.6°(MeOH, c=0.51).

11.9 g (11.0 mmol) diamine tartaric acid salt was suspended in 200 mL 2 N NaOH. After 15 min the reaction mixture was extracted with 750 mL ethyl acetate. The organic layer was washed with brine, dried with $Na_2SO_4$ and the solvents removed under reduced pressure to yield 7.82 g (21.6 mmol, 98%) of the enantiomerically pure amine 4.

e.)

Compound 4 (168 g, 0.46 mol) was dissolved in DCM (2 L) and the carbonyldiimidazole (81.1 g, 0.50 mol) was added in small portions over a period of 10 min at RT. The mixture was stirred for 2 h at RT. The TLC showed complete consumption of the starting material.

Then, N,N-Diethylethylenediamine (110 mL, 1.01 mol) was added over a period of 10 min at which the temperature increased to 27° C. The mixture was stirred at RT for 15 h and poured onto ice water (3 L). The pH was titrated to pH 8 by adding diluted HCl solution, the organic phase was separated and washed with water (2 L) twice. The solution was dried over sodium sulfate, filtered and the solvent was evaporated under reduced pressure. The remainder was diluted with diethyl ether, the precipitate was filtered off, washed with diethyl ether and dried in vacuo (188 g (0.40 mol, 85%) of colorless crystals identified as 1-(2-Dimethylamino-ethyl)-3-((2R,4aS,5R,10bS)-5-phenyl-9-trifluoromethyl-3,4,4a,5,6,10b-hexahydro-2H-pyrano[3,2-c]quinolin-2-ylmethyl)-urea.

The filtrate was cooled to 4° C. overnight and additional 18 g (0.04 g, 8%) of the desired product 5 were filtered off and dried in vacuo.

The combined fractions were redissolved in acetone (1 L), warmed to 40° C. and water (3 L) was added slowly. The mixture was cooled to 4° C. for 3 h, the precipitate formed was filtered off and dried for 3 d at 80° C. under reduced pressure. 192 g (0.40 mol, 87%) of compound 5 as a colorless solid were obtained. Analytics: m.p.: 123° C., $[\alpha]_D^{20}$=−85.6° (MeOH, c=1.07).

EXAMPLE 2

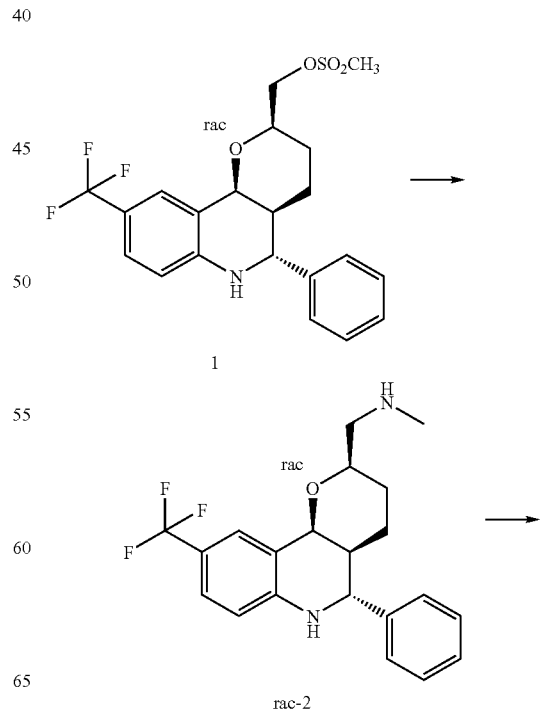

-continued

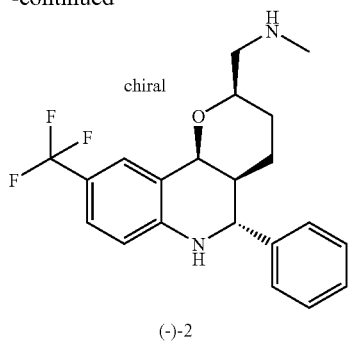

(−)-2

Compound 1 (3.9 g, 8.83 mmol) was added into a methylamine solution (40 mL, 33% solution in ethanol) and the reaction mixture was stirred overnight at 100° C. For completion of the reaction additional methylamine (20 mL, 33% solution in ethanol) was added and the reaction mixture was stirred overnight at 100° C. The reaction mixture was cooled down to room temperature. During the cooling precipitation occurred. The resulting crystals were collected by filtration and dried at 35° C. in a vacuum drying oven. Yield: 1.17 g clear crystals. The remaining residue solution was concentrated under reduced pressure and treated with t-butyl methyl ether. The resulting crystals were collected by filtration and dried at 35° C. in a vacuum drying oven. Yield: 1.6 g clear crystals. The material from both crystallization was combined, resulting in 2.77 g (7.35 mmol, 83% yield) compound rac-2.

Compound rac-2 (0.93 g, 2.47 mmol) was dissolved in 15 mL ethanol and heated to reflux. 0.45 g (1.24 mmol) (2R,3R)-(−)-Di-O-benzoyl tartaric acid and 25 mL ethanol were added and the solution heated to reflux. The solution was filtered and the filter washed with 5 mL hot ethanol. The filtrate was allowed to stand for about 18 h at room temperature. During that time precipitation started. The crystals were collected by filtration, washed with a little amount of cold ethanol and then air-dried to give compound (−)-2 (0.42 g, 0.38 mmol) as diamine tartaric acid salt. Analytics: m.p. 200-203° C., $\alpha_D$=−105.8° (methanol).

A sample of the crystals was treated with 1 N NaOH, extracted with ethyl acetate and the solvent removed under reduced pressure. The optical purity of resulting compound (−)-2 was determined >98% by chiral HPLC.

EXAMPLE 3

Form A1 (stable polymorph) of 1-(2-Dimethylamino-ethyl)-3-((2R,4aS,5R,10bS)-5-phenyl-9-trifluoromethyl-3,4,4a,5,6,10b-hexahydro-2H-pyrano[3,2-c]quinolin-2-ylmethyl)-urea I) Seeding Crystals Under gentle warming the compound of 1-(2-Dimethylamino-ethyl)-3-((2R,4aS,5R,10bS)-5-phenyl-9-trifluoromethyl-3,4,4a,5,6,10b-hexahydro-2H-pyrano[3,2-c]quinolin-2-ylmethyl)-urea (1 g) was dissolved in 2-propanole (50 mL). All solvents were removed under reduced pressure. Under gentle warming a part of the resulting residue (0.5 g) was dissolved in acetone (4.5 mL). Water (4.0 mL) was added until the crystallization started. Additional water (2 mL) was added and the mixture was allowed to stand for 18 h at 0° C. (ice-bath). The resulting crystals were collected by filtration, washed with cold water and dried (80° C., ~0.3 torr) to receive clear crystals (0.45 g) of 1-(2-Dimethylamino-ethyl)-3-((2R,4aS,5R,10bS)-5-phenyl-9-trifluoromethyl-3,4,4a,5,6,10b-hexahydro-2H-pyrano[3,2-c]quinolin-2-ylmethyl)-urea. The crystals were used as seeding crystals (see section II).

II) Crystallization

Under gentle warming the compound of formula I (271.6 g) was dissolved in acetone (2 L). All solvents were removed under reduced pressure. The remaining residue (261 g) was dissolved in warm acetone (1 L). Water (3 L) was added slowly. When approx. 2.6 L water was added the beforehand clear solution turned misty. Seeding crystals (see section 1) were added and the mixture was allowed to stand for 3 h at 0° C. (ice-bath). The resulting crystals were collected by filtration and washed with cold water. The obtained crystals were dried for 3 d (80° C., ~1 torr) to give clear crystals (243 g) of the 1-(2-Dimethylamino-ethyl)-3-((2R,4aS,5R,10bS)-5-phenyl-9-trifluoromethyl-3,4,4a,5,6,10b-hexahydro-2H-pyrano[3,2-c]quinolin-2-ylmethyl)-urea as form A1.

XRPD Diffractogram (FIG. 1)

No., d/Å, 2θ±0.1, I/Io 1, 13.90, 6.35, 100; 2, 11.32, 7.81, 52; 3, 9.74, 9.07, 36; 4, 8.51, 10.38, 27; 5, 6.41, 13.80, 37; 6, 5.40, 16.39, 58; 7, 4.86, 18.22, 94; 8, 4.78, 18.55, 49; 9, 4.35, 20.39, 55; 10, 4.30, 20.65, 54

Raman Spectrum (FIG. 4)

wavenumber/cm$^{-1}$

3059±1.5 m, 2948±1.5 m, 2922±1.5 m, 2897±1.5 m, 2867±1.5 m, 2783±1.5 m, 1663±1.5 w, 1627±1.5 s, 1606±1.5 m, 1587±1.5 w, 1457±1.5 m, 1374±1.5 w, 1346±1.5 w, 1330±1.5 m, 1320±1.5 w, 1264±1.5 w, 1204±1.5 w, 1190±1.5 w, 1159±1.5 w, 1132±1.5 w, 1083±1.5 w, 1064±1.5 m, 1029±1.5 m, 1002±1.5 m, 955±1.5 w, 925±1.5 w, 881±1.5 m, 831±1.5 m, 797±1.5 m, 761±1.5 m, 746±1.5 m, 674±1.5 m, 621±1.5 w, 507±1.5 w, 456±1.5 w,

IR Spectrum (FIG. 7)

wavenumber/cm$^{-1}$

3452±1.5 w, 3301±1.5 m, 3063±1.5 w, 3033±1.5 w, 2945±1.5 m, 2923±1.5 w, 2896±1.5 w, 2863±1.5 w, 2830±1.5 w, 1660±1.5 m, 1627±1.5 s, 1524±1.5 w, 1496±1.5 w, 1455±1.5 m, 1320±1.5 s, 1262±1.5 m, 1202±1.5 w, 1189±1.5 m, 1161±1.5 m, 1129±1.5 m, 1104±1.5 s, 1070±1.5 m, 1064±1.5 w, 1029±1.5 m, 952±1.5 w, 941±1.5 w, 904±1.5 w, 880±1.5 w, 867±1.5 m, 833±1.5 m, 827±1.5 m, 760±1.5 m, 707±1.5 m, 672±1.5 w, 644±1.5 w, 635±1.5 m, 505±1.5 w, 455±1.5 w

EXAMPLE 4

Form A2 (Metastable Polymorph) of 1-(2-Dimethylamino-ethyl)-3-((2R,4aS,5R,10bS)-5-phenyl-9-trifluoromethyl-3,4,4a,5,6,10b-hexahydro-2H-pyrano[3, 2-c]quinolin-2-ylmethyl)-urea 1-(2-Dimethylamino-ethyl)-3-((2R,4aS,5R,10bS)-5-phenyl-9-trifluoromethyl-3,4,4a,5,6,10b-hexahydro-2H-pyrano[3,2-c]quinolin-2-ylmethyl)-urea (50 mg, 0.105 mmol) form A1 was dispensed in n-heptane (200 mL) and the slurry stirred at room temperature for 5 days. The slurry was transferred into a petri dish and dried in a cabinet drier in air at 40° C. for 1 day. The recrystallized substance was identified as 1-(2-Dimethylamino-ethyl)-3-((2R,4aS,5R,10bS)-5-phenyl-9-trifluoromethyl-3,4,4a,5,6,10b-hexahydro-2H-pyrano[3, 2-c]quinolin-2-ylmethyl)-urea in the polymorphic form A2.

XRPD Diffractogram (FIG. 2)

No., d/Å, 2θ±0.1, I/Io
1, 23.71, 3.7, 100; 2, 19.44, 4.5, 54; 3, 15.41, 5.7, 37; 4, 12.00, 7.4, 27; 5, 5.96, 14.8, 25; 6, 5.36, 16.5, 28; 7, 4.65, 19.1, 93; 8, 4.56, 19.5, 27; 9, 4.25, 20.9, 41; 10, 4.20, 21.1, 27

Raman Spectrum (FIG. 5)
wavenumber/cm$^{-1}$
3060±1.5 m, 2946±1.5 m, 2865±1.5 w, 2779±1.5 w, 1624±1.5 m, 1606±1.5 m, 1587±1.5 m, 1443±1.5 m, 1328±1.5 m, 1261±1.5 w, 1179±1.5 w, 1157±1.5 w, 1063±1.5 w, 1030±1.5 m, 1002±1.5 m, 896±1.5 m, 831±1.5 w, 800±1.5 w, 764±1.5 m, 745±1.5 w, 674±1.5 w, 621±1.5 w, 504±1.5 w IR Spectrum (FIG. 8)
wavenumber/cm$^{-1}$
3451±1.5 w, 3306±1.5 m, 3064±1.5 w, 3032±1.5 w, 2943±1.5 m, 2924±1.5 w, 2896±1.5 w, 2861±1.5 w, 2828±1.5 w, 1658±1.5 m, 1626±1.5 s, 1570±1.5 m, 1524±1.5 m, 1496±1.5 w, 1455±1.5 m, 1320±1.5 s, 1261±1.5 m, 1202±1.5 w, 1188±1.5 m, 1160±1.5 m, 1131±1.5 m, 1104±1.5 s, 1071±1.5 m, 1064±1.5 m, 1029±1.5 m, 954±1.5 w, 941±1.5 w, 904±1.5 w, 880±1.5 w, 869±1.5 w, 833±1.5 m, 761±1.5 m, 706±1.5 m, 672±1.5 w, 645±1.5 w, 635±1.5 m, 503±1.5 w, 455±1.5 w.

EXAMPLE 5

Form A3 (Metastable Polymorph) of 1-(2-Dimethylamino-ethyl)-3-((2R,4aS,5R,10bS)-5-phenyl-9-trifluoromethyl-3,4,4a,5,6,10b-hexahydro-2H-pyrano[3,2-c]quinolin-2-ylmethyl)-urea (100 mg, 0.210 mmol) form A1 was dispensed in n-heptane (35 mL) and the slurry stirred at room temperature for 5 days. The precipitate was filtered off using a paper filter and immediately dried in vacuo. The substance was identified as 1-(2-Dimethylamino-ethyl)-3-((2R,4aS,R5,10bS)-5-phenyl-9-trifluoromethyl-3,4,4a,5,6,10b-hexahydro-2H-pyrano[3,2-c]quinolin-2-ylmethyl)-urea in the polymorphic form A3.

XRPD Diffractogram
No., d/Å, 2θ±0.1, I/Io
1, 23.81, 3.7, 100; 2, 19.74, 4.5, 68; 3, 15.56, 5.7, 55; 4, 11.96, 7.4, 45; 5, 9.99, 8.8, 30; 6, 9.22, 9.6, 28; 7, 8.57, 10.3, 25; 8, 7.87, 11.2, 26; 9, 7.41, 11.9, 30; 10, 6.41, 13.8, 26; 11, 5.96, 14.9, 34; 12, 5.80, 15.3, 28; 13, 5.35, 16.6, 35; 14, 5.21, 17.0, 24; 15, 4.95, 17.9, 28; 16, 4.81, 18.4, 32; 17, 4.64, 19.1, 75; 18, 4.43, 20.0, 25; 19, 4.24, 21.0, 43; 20, 4.15, 21.4, 30; 21, 3.95, 22.5, 15; 22, 3.75, 23.7, 20; 23, 3.65, 24.3, 19; 24, 3.45, 25.8, 11; 25, 3.38, 26.4, 15; 26, 3.26, 27.4, 11; 27, 3.03, 29.4, 9; 28, 2.87, 31.2, 7; 29, 2.74, 32.6, 8; 30, 2.44, 36.9, 5; 31, 2.32, 38.8, 6; 32, 2.18, 41.3, 6; 33, 2.13, 42.4, 6; 34, 3.00, 29.8, 9; 35, 3.60, 24.7, 17; 36, 7.31, 12.1, 29; 37, 5.04, 17.6, 21; 38, 3.86, 23.0, 14; 39, 4.32, 20.6, 21.

Ramen Spectrum (FIG. 6)
Wavenumber/cm$^{-1}$
3066±1.5 m, 3060±1.5 s, 2946±1.5 s, 2863±1.5 m, 2779±1.5 w, 1624±1.5 s, 1606±1.5 m, 1444±1.5 m, 1328±1.5 m, 1261±1.5 m, 1179±1.5 m, 1157±1.5 m, 1063±1.5 w, 1030±1.5 m, 1002±1.5 s, 896±1.5 m, 831±1.5 m, 800±1.5 m, 764±1.5 m, 674±1.5 m, 621±1.5 m, 504±1.5 m IR Spectrum (FIG. 9)
Wavenumber/cm$^{-1}$
3306±1.5 m, 2943±1.5 m, 2861±11.5 m, 1658±11.5 m, 1626±11.5 s, 1570±1.5 m, 1525±1.5 m, 1455±1.5 m, 1320±1.5 s, 1261±1.5 m, 1188±1.5 m, 1160±1.5 m, 1131±1.5 m, 1104±1.5 m, 1064±1.5 m, 1029±1.5 m, 833±1.5 m, 761±1.5 m, 706±1.5 m, 635±1.5 m

The invention claimed is:
1. A process for the manufacture of an enantiomerically enriched or pure compound of formula I

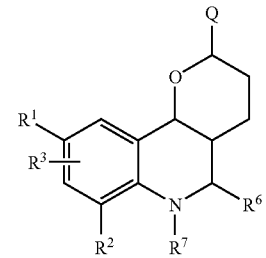

wherein
$R^1$, $R^2$, $R^3$ are each, independently of one another, H, A, Aryl, Heteroaryl, Hal, —(CY$_2$)$_n$—SA, —(CY$_2$)$_n$—SCF$_3$, —(CY$_2$)—SCN, —(CY$_2$)$_n$—CF$_3$, —(CY$_2$)—OCF$_3$, R, Cycloalkyl, —SCH$_3$, —SCN, —CF$_3$, —OCF$_3$, —OA, —(CY$_2$)$_n$—OH, —(CY$_2$)$_n$—CO$_2$R, —(CY$_2$)$_n$—CN, —(CY$_2$)$_n$-Hal, —(CY$_2$)$_n$—NR$_2$, (CY$_2$)$_n$—OA, (CY$_2$)$_n$—OCOA, —SCF$_3$, (CY$_2$)$_n$—CONR$_2$, —(CY$_2$)$_n$—NHCOA, —(CY$_2$)$_n$—NHSO$_2$A, SF$_5$, Si(CH$_3$)$_3$, CO—(CY$_2$)$_n$—CH$_3$, —(CY$_2$)$_n$—N-Pyrrolidone, (CH$_2$)$_n$NRCOOR, NRCOOR, NCO, (CH$_2$)$_n$COOR, NCOOR, (CH$_2$)$_n$OH, NR(CH$_2$)$_n$NR$_2$, C(OH)R$_2$, NR(CH$_2$)$_n$OR, NCOR, (CH$_2$)$_n$Aryl, (CH$_2$)$_n$Heteroaryl, (CH$_2$)$_n$R$^1$, (CH$_2$)$_n$X(CH$_2$)$_n$Aryl, (CH$_2$)$_n$X(CH$_2$)$_n$Heteroaryl, (CH$_2$)$_n$CONR$_2$, XCONR(CH$_2$)$_n$NR$_2$, N[(CH$_2$)$_n$XCOOR]CO(CH$_2$)$_n$Aryl, N[(CH$_2$)$_n$XR]CO(CH$_2$)$_n$Aryl, N[(CH$_2$)$_n$XR]CO(CH$_2$)$_n$XAryl, N[(CH$_2$)$_n$XR]SO$_2$(CH$_2$)$_n$Aryl, N[(CH$_2$)$_n$NRCOOR]CO(CH$_2$)$_n$Aryl, N[(CH$_2$)$_n$NR$_2$]CO(CH$_2$)$_n$Aryl, N[(CH$_2$)$_n$NR$_2$]CO(CH$_2$)$_n$NRAryl, N[(CH$_2$)$_n$NR$_2$]SO$_2$(CH$_2$)$_n$Aryl, N[(CH$_2$)$_n$XR]CO(CH$_2$)$_n$Heteroaryl, N[(CH$_2$)$_n$XR]CO(CH$_2$)$_n$XHeteroaryl, N[(CH$_2$)$_n$XR]SO$_2$(CH$_2$)$_n$Heteroaryl, N[(CH$_2$)$_n$NRCOOR]CO(CH$_2$)$_n$Heteroaryl, N[(CH$_2$)$_n$NR$_2$]CO(CH$_2$)$_n$Heteroaryl, or N[(CH$_2$)$_n$NR$_2$]CO(CH$_2$)$_n$NRHeteroaryl, and R$^1$ and R$^3$ together also may be —N—C(CF$_3$)=N—, —N—CR=N— or —N—N=N—, and wherein non-adjacent groups CY$_2$ can be replaced by X,
Y is H, A, Hal, OR, E-R$^1$,
E is —NR$^1$SO$_2$—, —NR$^1$CO—, NR$^1$CONR$^1$—, —NR$^1$COO—, —NR$^1$CS—, —NR$^1$CSNR$^1$—, —NR$^1$COS—, NR$^1$CSO—, —NR$^1$CSS or —NR$^1$—,
A is Alkyl or Cycloalkyl, wherein one or more H-atoms can be replaced by Hal,
Hal is F, Cl, Br or I,
R is H or A, in the case of geminal groups R together also —(CH$_2$)$_5$—, —(CH$_2$)$_4$—or —(CH$_2$)$_n$—X—(CH$_2$)$_n$, or —(CH$_2$)$_n$—Z—(CH$_2$)$_n$,
X is O, S or NR$^1$,
Q is CH$_2$-E-(CH$_2$)$_p$R$^1$,
Z is CH$_2$, X, CHCONH$_2$, CH(CH$_2$)$_n$NR$^1$COOR$^1$, CHNR$^1$COOR$^1$, NCHO, CHCON(R$^1$)$_2$, CH(CH$_2$)$_n$COOR$^1$, NCOOR$^1$, CH(CH$_2$)$_n$OH, N(CH$_2$)$_n$OH, CHNH$_2$, CH(CH$_2$)$_n$NR$^1$$_2$, CH(CH$_2$)$_n$NR$^1$$_2$, C(OH)R$^1$, CHNCOR$^1$, NCOR$^1$, N(CH$_2$)$_n$Aryl, N(CH$_2$)$_n$Heteroaryl, CHR$^1$, NR$^1$, CH(CH$_2$)$_n$Aryl, CH(CH$_2$)$_n$Heteroaryl, CH(CH$_2$)$_n$R$^1$, N(CH$_2$)$_n$COOR$^1$, CH(CH$_2$)$_n$X(CH$_2$)$_n$Aryl, CH(CH$_2$)$_n$X(CH$_2$)$_n$Heteroaryl, N(CH$_2$)$_n$CON(R$^1$)$_2$, NSO$_2$R$^1$, CHSO$_2$N(R$^1$)$_2$, XCONR(CH$_2$)$_n$N(R$^1$)$_2$, NCO(CH$_2$)$_n$Aryl, NCO(CH$_2$)$_n$XAryl, NSO$_2$(CH$_2$)$_n$Aryl, NCO(CH$_2$)$_n$Aryl, NCO(CH$_2$)$_n$NR$^1$Aryl, NCO(CH$_2$)$_n$Heteroaryl, NCO(CH$_2$)$_n$XHeteroaryl, NSO$_2$(CH$_2$)$_n$Heteroaryl, NCO(CH$_2$)$_n$NR$^1$Heteroaryl, N(CH$_2$)$_n$NR$_2$CH, CHO(CH$_2$)$_n$N(R$^1$)$_2$, CHX(CH$_2$)$_n$N(R$^1$)$_2$, or NCO(CH$_2$)$_n$NR$_2$, R$^6$ is unsubstituted Aryl or Heteroaryl, or Aryl or Heteroaryl which is substituted in at least one position by Hal, NO$_2$, CN, OR, A, —(CY$_2$)$_n$—OR, —OCOR, —(CY$_2$)$_n$—CO$_2$R, —(CY$_2$)$_n$—CN, —NCOR, —COR, or —(CY$_2$)$_n$—NR$_2$, or by Aryl or Heteroaryl which also may be substituted by Hal, NO$_2$, CN, A, OR, OCOR, COR, NR$_2$, CF$_3$, OCF$_3$, or OCH(CF$_3$)$_2$, R$^7$ is (C=O)—R, (C=O)—NR$_2$, (C=O)—OR, H or A, n is 0, 1, 2, 3, 4, 5, 6 or 7, p is 0, 1, 2, 3, 4, or 5, and s is 0, 1, 2, 3 or 4, or a pharmaceutically acceptable tautomer, or salt thereof, said process comprising:

a) reacting enantiomerically pure (2R,3R)-(—)-Di-O-benzoyl tartaric acid with a racemic or non-enantiomerically pure compound of formula IA

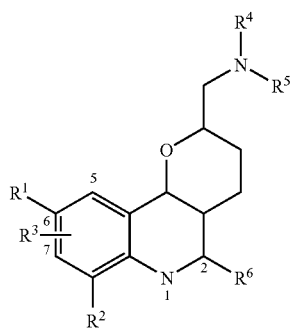

wherein

R$^1$, R$^2$, R$^3$ and R$^6$ are as defined above,

R$^4$, R$^5$ are each, independently of one another, T-R$^1$, and

T is —SO$_2$—, —CO—, —CONR$^1$—, —COO—, —CS—, —CSNR$^1$—, —COS—, —CSO—, —CSS or a single bond, whereby a crystalline complex is formed;

b) said crystalline complex is isolated and treated with a base to obtain an enantiomerically further enriched or pure compound of formula IA;

and c) optionally the enantiomerically further enriched or pure compound of formula IA is transformed into a further compound of formula I.

2. The process according to claim 1, wherein R$^4$ and R$^5$ of formula IA are both H.

3. The process according to claim 1, wherein R$^4$ is H and R$^5$ is methyl.

4. The process according to claim 1, wherein said enantiomerically enriched or pure compound is a compound of formula IB

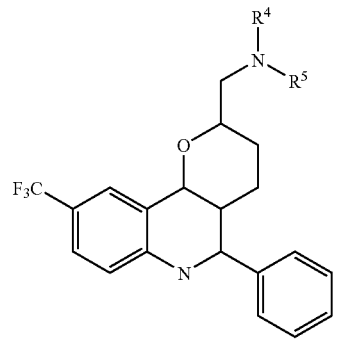

wherein R$^4$ and R$^5$ are both H or R$^4$ is H and R$^5$ is methyl.

5. The process according to claim 1, wherein the compound of formula I is 1-(2-Dimethylamino-ethyl)-3-((2R,4aS,5R,10bS)-5-phenyl-9-trifluoromethyl-3,4,4a,5,6,10b-hexahydro-2H-pyrano[3,2-c]quinolin-2-ylmethyl)-urea.

6. The process according to claim 1, wherein the compound of formula I is 1-(2-Dimethylamino-ethyl)-3-((2R,4aS,5R,10bS)-5-phenyl-9-trifluoromethyl-3,4,4a,5,6,10b-hexahydro-2H-pyrano[3,2-c]quinolin-2-ylmethyl)-urea in the crystalline Form A1 having the following data:

XRPD diffractogram

No., d/Å, 2θ±0.1, I/Io 1, 13.90, 6.35, 100;
2, 11.32, 7.81, 52;
3, 9.74, 9.07, 36;
4, 8.51, 10.38, 27;
5, 6.41, 13.80, 37;
6, 5.40, 16.39, 58;
7, 4.86, 18.22, 94;
8, 4.78, 18.55, 49;
9, 4.35, 20.39, 55;
10, 4.30, 20.65, 54

Raman spectrum wavenumber/cm$^{-1}$

3059±1.5 m, 2948±1.5 m, 2922±1.5 m, 2897±1.5 m, 2867±1.5 m, 2783±1.5 m, 1663±1.5 w, 1627±1.5 s, 1606±1.5 m, 1587±1.5 w, 1457±1.5 m, 1374±1.5 w, 1346±1.5 w, 1330±1.5 m, 1320±1.5 w, 1264±1.5 w, 1204±1.5 w, 1190±1.5 w, 1159±1.5 w, 1132±1.5 w, 1083±1.5 w, 1064±1.5 m, 1029±1.5 m, 1002±1.5 m, 955±1.5 w, 925±1.5 w, 881±1.5 m, 831±1.5 m, 797±1.5 m, 761±1.5 m, 746±1.5 m, 674±1.5 m, 621±1.5 w, 507±1.5 w, 456±1.5 w,

IR spectrum wavenumber/cm$^{-1}$

3452±1.5 w, 3301±1.5 m, 3063±1.5 w, 3033±1.5 w, 2945±1.5 m, 2923±1.5 w, 2896±1.5 w, 2863±1.5 w, 2830±1.5 w, 1660±1.5 m, 1627±1.5 s, 1524±1.5 w, 1496±1.5 w, 1455±1.5 m, 1320±1.5 s, 1262±1.5 m, 1202±1.5 w, 1189±1.5 m, 1161±1.5 m, 1129±1.5 m, 1104±1.5 s, 1070±1.5 m, 1064±1.5 w, 1029±1.5 m, 952±1.5 w, 941±1.5 w, 904±1.5 w, 880±1.5 w, 867±1.5 w, 833±1.5 m, 827±1.5 m, 760±1.5 m, 707±1.5 m, 672±1.5 w, 644±1.5 w, 635±1.5 m, 505±1.5 w, 455±1.5 w.

7. The process according to claim 1, wherein the compound of formula I is 1-(2-Dimethylamino-ethyl)-3-((2R,4aS,5R,10bS)-5-phenyl-9-trifluoromethyl-3,4,4a,5,6,10b-hexahydro-2H-pyrano[3,2-c]quinolin-2-ylmethyl)-urea in the crystalline Form A2 having the following data:

XRPD diffractogram
No., d/Å, 2θ±0.1, I/Io
1, 23.71, 3.7, 100;
2, 19.44, 4.5, 54;
3, 15.41, 5.7, 37;
4, 12.00, 7.4, 27;
5, 5.96, 14.8, 25;
6, 5.36, 16.5, 28;
7, 4.65, 19.1, 93;
8, 4.56, 19.5, 27;
9, 4.25, 20.9, 41;
10, 4.20, 21.1, 27
Raman spectrum
wavenumber/cm$^{-1}$
3060±1.5 m, 2946±1.5 m, 2865±1.5 w, 2779±1.5 w, 1624±1.5 m, 1606±1.5 m, 1587±1.5 m, 1443±1.5 m, 1328±1.5 m, 1261±1.5 w, 1179±1.5 w, 1157±1.5 w, 1063±1.5 w, 1030±1.5 m, 1002±1.5 m, 896±1.5 m, 831±1.5 w, 800±1.5 w, 764±1.5 m, 745±1.5 w, 674±1.5 w, 621±1.5 w, 504±1.5 w
IR spectrum
wavenumber/cm$^{-1}$
3451±1.5 w, 3306±1.5 m, 3064±1.5 w, 3032±1.5 w, 2943±1.5 m, 2924±1.5 w, 2896±1.5 w, 2861±1.5 w, 2828±1.5 w, 1658±1.5 m, 1626±1.5 s, 1570±1.5 m, 1524±1.5 m, 1496±1.5 w, 1455±1.5 m, 1320±1.5 s, 1261±1.5 m, 1202±1.5 w, 1188±1.5 m, 1160±1.5 m, 1131±1.5 m, 1104±1.5 s, 1071±1.5 m, 1064±1.5 m, 1029±1.5 m, 954±1.5 w, 941±1.5 w, 904±1.5 w, 880±1.5 w, 869±1.5 w, 833±1.5 m, 761±1.5 m, 706±1.5 m, 672±1.5 w, 645±1.5 w, 635±1.5 m, 503±1.5 w, 455±1.5 w.

8. The process according to claim 1, wherein the compound of formula I is 1-(2-Dimethylamino-ethyl)-3-((2R,4aS,5R,10bS)-5-phenyl-9-trifluoromethyl-3,4,4a,5,6,10b-hexahydro-2H-pyrano[3,2-c]quinolin-2-ylmethyl)-urea in the crystalline Form A3 having the following data:
Raman spectrum
Wavenumber/cm$^{-1}$
3066±1.5 m, 3060±1.5 s, 2946±1.5 s, 2863±1.5 m, 2779±1.5 w, 1624±1.5 s, 1606±1.5 m, 1444±1.5 m, 1328±1.5 m, 1261±1.5 m, 1179±1.5 m, 1157±1.5 m, 1063±1.5 w, 1030±1.5 m, 1002±1.5 s, 896±1.5 m, 831±1.5 m, 800±1.5 m, 764±1.5 m, 674±1.5 m, 621±1.5 m, 504±1.5 m
IR spectrum
Wavenumber/cm$^{-1}$
3306±1.5 m, 2943±1.5 m, 2861±1.5 m, 1658±1.5 m, 1626±1.5 s, 1570±1.5 m, 1525±1.5 m, 1455±1.5 m, 1320±1.5 s, 1261±1.5 m, 1188±1.5 m, 1160±1.5 m, 1131±1.5 m, 1104±1.5 s, 1064±1.5 m, 1029±1.5 m, 833±1.5 m, 761±1.5 m, 706±1.5 m, 635±1.5 m.

9. The process according to claim 1, wherein p is 1 or 2, and s is 0.

10. The process according to claim 1, wherein said compound of formula I is a compound of the following formula:

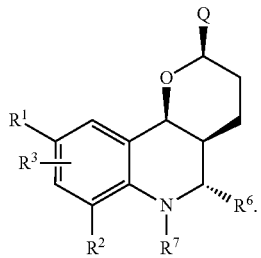

11. The process according to claim 1, wherein
$R^1$ is A, $CF_3$, $OCF_3$, SA, SCN, CHCN, —OCOA, Hal, $SCF_3$, preferably also t-butyl, —$CH(CH_3)CH_2CH_3$, isopropyl, ethyl or methyl,
$R^2$ is H, Hal, A or OA,
$R^3$ is H, A, or F,
$R^6$ is phenyl, 2-, 3- or 4-pyridyl, pyrimidyl, furyl or thienyl, which in each case is unsubstituted or mono- or polysubstituted by Hal, CN, $NO_2$, OH, $CF_3$, $OCH(CF_3)_2$, $OCOCH_3$ or A, and
$R^7$ is H or A.

12. The process according to claim 1, wherein
$R^1$ is t-butyl, isopropyl, ethyl, $CF_3$, methyl, Br, Cl, $SCF_3$, $CH(CH_3)CH_2CH_3$, n-propyl, $OCH_3$, $SCH_3$, n-butyl, —SCN, CHCN,
$R^2$ is Br, cyclopropyl, or $OCH_3$,
$R^3$ is H or A, and
$R^7$ is H.

13. The process according to claim 1, wherein
$R^1$ is t-butyl, isopropyl, ethyl or $CF_3$,
$R^2$ is H or F, and
$R^3$ is H.

14. The process according to claim 4, wherein said compound of formula IA is a compound of the following formula:

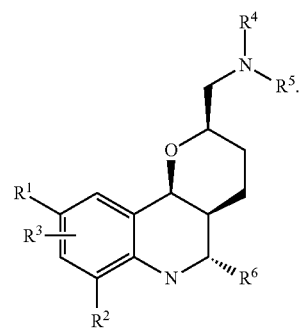

15. The process according to claim 1, wherein said compound of formula I is a compound of the following formula IB:

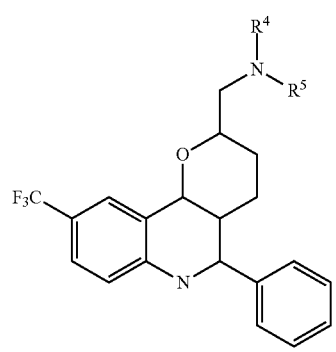

16. The process according to claim 15, wherein said compound of formula IB is a compound of the following formula:

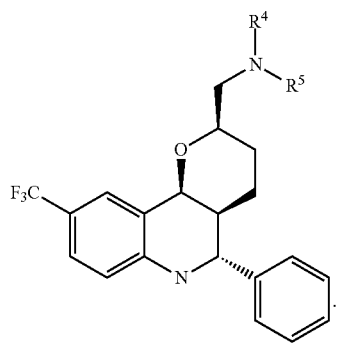

17. A process according to claim 1, wherein the enantiomerically further enriched or pure compound of formula IA has an enantiomeric purity of higher than 98%.

18. The process according to claim 5, further comprising
d) crystallizing the compound 1-(2-Dimethylaminoethyl)-3-((2R,4aS,5R,10bS)-5-phenyl-9-trifluoromethyl-3,4,4a,5,6,10b-hexahydro-2H-pyrano[3,2-c] quinolin-2-ylmethyl)-urea in a solvent to obtain crystalline form A1, A2, or A3, substantially free of other forms of the compound; and
e) optionally recrystallizing the crystalline form formed in d), or a mixture of any forms of the compound formed in c) and d), in a solvent to obtain a different crystalline form, substantially free of other forms of the compound.

19. The process according to claim 18, wherein in d) the compound is crystallized in acetone, acetonitrile, an acetone/water mixture, or an acetonitrile/water mixture.

20. The process according to claim 18, wherein in e) the crystalline form or mixture is recrystallized in n-heptane.

21. The process according to claim 19, wherein in e) the crystalline form or mixture is recrystallized in n-heptane.

* * * * *

UNITED STATES PATENT AND TRADEMARK OFFICE
CERTIFICATE OF CORRECTION

PATENT NO. : 8,198,452 B2
APPLICATION NO. : 12/305524
DATED : June 12, 2012
INVENTOR(S) : Kai Schiemann et al.

It is certified that error appears in the above-identified patent and that said Letters Patent is hereby corrected as shown below:

Column 22, Line 21 reads: "$SCF_3$, $-(CY_2)-SCN$, $-(CY_2)_n-CF_3$, $-(CY_2)-$" should read --$SCF_3$, $-(CY_2)_n-SCN$, $-(CY_2)_n-CF_3$, $-(CY_2)_n-$ --.

Signed and Sealed this
Twenty-seventh Day of November, 2012

David J. Kappos
*Director of the United States Patent and Trademark Office*